(12) United States Patent
Borchert et al.

(10) Patent No.: US 6,673,589 B2
(45) Date of Patent: Jan. 6, 2004

(54) α-AMYLASE MUTANTS

(75) Inventors: Torben Vedel Borchert, Copenhagen Ø (DK); Allan Svendsen, Birkerød (DK); Carsten Andersen, Vaerloese (DK); Bjarne Nielsen, Virum (DK); Torben Lauesgaard Nissen, Frederiksberg C (DK); Søren Kjærulff, Vanløse (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/769,864

(22) Filed: Jan. 25, 2001

(65) Prior Publication Data

US 2001/0039253 A1 Nov. 8, 2001

Related U.S. Application Data

(62) Division of application No. 09/183,412, filed on Oct. 30, 1998, now Pat. No. 6,204,232.
(60) Provisional application No. 60/064,662, filed on Nov. 6, 1997, and provisional application No. 60/093,234, filed on Jul. 17, 1998.

(30) Foreign Application Priority Data

Oct. 30, 1997 (DK) ............................................. 1240/97
Jul. 14, 1998 (DK) .................................. PA 1998 00936

(51) Int. Cl.[7] .............................. C12N 9/28; C11D 3/00
(52) U.S. Cl. ...................... 435/202; 510/226; 510/236; 510/320; 510/396
(58) Field of Search .......................... 435/202; 510/226, 510/236, 320, 396

(56) References Cited

U.S. PATENT DOCUMENTS

| | | | | |
|---|---|---|---|---|
| 5,736,499 A | * | 4/1998 | Mitchinson et al. | 510/392 |
| 6,143,708 A | * | 11/2000 | Svendsen et al. | 510/226 |
| 6,187,576 B1 | * | 2/2001 | Svendsen et al. | 435/202 |

FOREIGN PATENT DOCUMENTS

| | | |
|---|---|---|
| WO | WO 90/11352 | 10/1990 |
| WO | WO 91/00353 | 1/1991 |
| WO | WO 95/10603 | 4/1995 |
| WO | WO 95/26397 | 10/1995 |
| WO | WO 95/35382 | 12/1995 |
| WO | WO 96/23873 | 8/1996 |
| WO | WO 96/23874 | 8/1996 |
| WO | WO 97/41213 | 11/1997 |

* cited by examiner

Primary Examiner—Rebecca E. Prouty
(74) Attorney, Agent, or Firm—Elias Lambiris; Jason Garbell

(57) ABSTRACT

The invention relates to a variant of a parent Termamyl-like α-amylase, which exhibits an alteration in at least one of the following properties relative to said parent α-amylase: i) improved pH stability at a pH from 8 to 10.5; and/or ii) improved $Ca^{2+}$ stability at pH 8 to 10.5, and/or iii) increased specific activity at temperatures from 10 to 60° C.

34 Claims, 7 Drawing Sheets

```
       1                                                                    50
1   HHNGTNGTMM  QYFEWHLPND  GNHWNRLRDD  ASNLRNRGIT  AIWIPPAWKG
2   ..NGTNGTMM  QYFEWYLPND  GNHWNRLRSD  ASNLKDKGIS  AVWIPPAWKG
3   HHNGTNGTMM  QYFEWYLPND  GNHWNRLRDD  AANLKSKGIT  AVWIPPAWKG
4   ....VNGTLM  QYFEWYTPND  GQHWKRLQND  AEHLSDIGIT  AVWIPPAYKG
5   ..ANLNGTLM  QYFEWYMPND  GQHWRRLQND  SAYLAEHGIT  AVWIPPAYKG
6   .AAPFNGTMM  QYFEWYLPDD  GTLWTKVANE  ANNLSSLGIT  ALWLPPAYKG 51                                                                  100
1   TSQNDVGYGA  YDLYDLGEFN  QKGTVRTKYG  TRSQLESAIH  ALKNNGVQVY
2   ASQNDVGYGA  YDLYDLGEFN  QKGTIRTKYG  TRNQLQAAVN  ALKSNGIQVY
3   TSQNDVGYGA  YDLYDLGEFN  QKGTVRTKYG  TRNQLQAAVT  SLKNNGIQVY
4   LSQSDNGYGP  YDLYDLGEFQ  QKGTVRTKYG  TKSELQDAIG  SLHSRNVQVY
5   TSQADVGYGA  YDLYDLGEFH  QKGTVRTKYG  TKGELQSAIK  SLHSRDINVY
6   TSRSDVGYGV  YDLYDLGEFN  QKGTVRTKYG  TKAQYLQAIQ  AAHAAGMQVY 101                                                                 150
1   GDVVMNHKGG  ADATENVLAV  EVNPNNRNQE  ISGDYTIEAW  TKFDFPGRGN
2   GDVVMNHKGG  ADATEMVRAV  EVNPNNRNQE  VSGEYTIEAW  TKFDFPGRGN
3   GDVVMNHKGG  ADGTEIVNAV  EVNRSNRNQE  TSGEYAIEAW  TKFDFPGRGN
4   GDVVLNHKAG  ADATEDVTAV  EVNPANRNQE  TSEEYQIKAW  TDFRFPGRGN
5   GDVVINHKGG  ADATEDVTAV  EVDPADRNRV  ISGEHLIKAW  THFHFPGRGS
6   ADVVFDHKGG  ADGTEWVDAV  EVNPSDRNQE  ISGTYQIQAW  TKFDFPGRGN 151                                                                 200
1   TYSDFKWRWY  HFDGVDWDQS  RQFQNRIYKF  RGDGKAWDWE  VDSENGNYDY
2   THSNFKWRWY  HFDGVDWDQS  RKLNNRIYKF  RGDGKGWDWE  VDTENGNYDY
3   NHSSFKWRWY  HFDGTDWDQS  RQLQNKIYKF  RGTGKAWDWE  VDTENGNYDY
4   TYSDFKWHWY  HFDGADWDES  RKI.SRIFKF  RGEGKAWDWE  VSSENGNYDY
5   TYSDFKWHWY  HFDGTDWDES  RKL.NRIYKF  ..QGKAWDWE  VSNENGNYDY
6   TYSSFKWRWY  HFDGVDWDES  RKL.SRIYKF  RGIGKAWDWE  VDTENGNYDY
```

Figure 1(a)

```
      201                                                         250
1   LMYADVDMDH  PEVVNELRRW  GEWYTNTLNL  DGFRIDAVKH  IKYSFTRDWL
2   LMYADIDMDH  PEVVNELRNW  GVWYTNTLGL  DGFRIDAVKH  IKYSFTRDWS
3   LMYADVDMDH  PEVIHELRNW  GVWYTNTLNL  DGFRIDAVKH  IKYSFTRDWL
4   LMYADVDYDH  PDVVAETKKW  GIWYANELSL  DGFRIDAAKH  IKFSFLRDWV
5   LMYADIDYDH  PDVAAEIKRW  GTWYANELQL  DGFRLDAVKH  IKFSFLRDWV
6   LMYADLDMDH  PEVVTELKNW  GKWYVNTTNI  DGFRLDAVKH  IKFSFFPDWL 251                                                         300
1   THVRNATGKE  MFAVAEFWKN  DLGALENYLN  KTNWNHSVFD  VPLHYNLYNA
2   IHVRSATGKN  MFAVAEFWKN  DLGAIENYLN  KTNWNHSVFD  VPLHYNFYNA
3   THVRNTTGKP  MFAVAEFWKN  DLGAIENYLN  KTSWNHSAFD  VPLHYNLYNA
4   QAVRQATGKE  MFTVAEYWQN  NAGKLENYLN  KTSFNQSVFD  VPLHFNLQAA
5   NHVREKTGKE  MFTVAEYWQN  DLGALENYLN  KTNFNHSVFD  VPLHYQFHAA
6   SYVRSQTGKP  LFTVGEYWSY  DINKLHNYIT  KTDGTMSLFD  APLHNKFYTA 301                                                         350
1   SNSGGNYDMA  KLLNGTVVQK  HPMHAVTFVD  NHDSQPGESL  ESFVQEWFKP
2   SKSGGNYDMR  QIFNGTVVQR  HPMHAVTFVD  NHDSQPEEAL  ESFVEEWFKP
3   SNSGGYYDMR  NILNGSVVQK  HPTHAVTFVD  NHDSQPGEAL  ESFVQQWFKP
4   SSQGGGYDMR  RLLDGTVVSR  HPEKAVTFVE  NHDTQPGQSL  ESTVQTWFKP
5   STQGGGYDMR  KLLNGTVVSK  HPLKSVTFVD  NHDTQPGQSL  ESTVQTWFKP
6   SKSGGAFDMR  TLMTNTLMKD  QPTLAVTFVD  NHDTEPGQAL  QSWVDPWFKP 351                                                         400
1   LAYALILTRE  QGYPSVFYGD  YYGIPTHS..  .VPAMKAKID  PILEARQNFA
2   LAYALTLTRE  QGYPSVFYGD  YYGIPTHG..  .VPAMKSKID  PILEARQKYA
3   LAYALVLTRE  QGYPSVFYGD  YYGIPTHG..  .VPAMKSKID  PLLQARQTFA
4   LAYAFILTRE  SGYPQVFYGD  MYGTKGTSPK  EIPSLKDNIE  PILKARKEYA
5   LAYAFILTRE  SGYPQVFYGD  MYGTKGDSQR  EIPALKHKIE  PILKARKQYA
6   LAYAFILTRQ  EGYPCVFYGD  YYGIPQYN..  .IPSLKSKID  PLLIARRDYA 401                                                         450
1   YGTQHDYFDH  HNIIGWTREG  NTTHPNSGLA  TIMSDGPGGE  KWMYVGQNKA
2   YGRQN.....  ..........  ..........  ..........  ..........
3   YGTQHDYFDH  HDIIGWTREG  NSSHPNSGLA  TIMSDGPGGN  KWMYVGKNKA
4   YGPQHDYIDH  PDVIGWTREG  DSSAAKSGLA  ALITDGPGGS  KRMYAGLKNA
5   YGAQHDYFDH  HDIVGWTREG  DSSVANSGLA  ALITDGPGGA  KRMYVGRQNA
6   YGTQHDYLDH  SDIIGWTREG  GTEKPGSGLA  ALITDGPGGS  KWMYVGKQHA
```

Figure 1 (b)

```
      451                                                         500
1  GQVWHDITGN KPGTVTINAD GWANFSVNGG SVSIWVKR.. ..........
2  .......... .......... .......... .......... ..........
3  GQVWRDITGN RTGTVTINAD GWGNFSVNGG SVSVWVKQ.. ..........
4  GETWYDITGN RSDTVKIGSD GWGEFHVNDG SVSIYVQ... ..........
5  GETWHDITGN RSEPVVINSE GWGEFHVNGG SVSIYVQR.. ..........
6  GKVFYDLTGN RSDTVTINSD GWGEFKVNGG SVSVWVPRKT TVSTIARPIT 501                519
1  .......... .........
2  .......... .........
3  .......... .........
4  .......... .........
5  .......... .........
6  TRPWTGEFVR WTEPRLVAW
```

Figure 1 (c)

```
       1                                                                  50
1  MKFVLLLSLI  GFCWAQYDPH  TSDG.RTAIV  HLFEWRWVDI  AKECERYLAP
2  .....LLSLI  GFCWAQYDPH  TADG.RTAIV  HLFEWRWADI  AKECERYLAP
3  ..........  .....QYAPQ  TQSG.RTDIV  HLFEWRWVDI  ALECERYLGP
4  MKFFLLLFTI  GFCWAQYSPN  TQQG.RTSIV  HLFEWRWVDI  ALECERYLAP
5  MKLNKIITTA  GLSLGLLLPS  IATATPTTFV  HLFEWNWQDV  AQECEQYLGP 51                                                                 100
1  KGFGGVQVSP  PNENVVVHNP  SRPWWERYQP  ISYKICTRSG  NEDEFRDMVT
2  KGFGGVQVSP  PNENIIINNP  SRPWWERYQP  ISYKICSRSG  NENEFKDMVT
3  KGFGGVQVSP  PNENVVVTNP  SRPWWERYQP  VSYKLCTRSG  NENEFRDMVT
4  KGFGGVQVSP  PNENVAIYNP  FRPWWERYQP  VSYKLCTRSG  NEDEFRNMVT
5  KGYAAVQVSP  PNEHI....T  GSQWWTRYQP  VSYELQSRGG  NRAQFIDMVN 101                                                                150
1  RCNNVGVRIY  VDAVINHMCG  AGNPAGTSST  CGSYLNPNNR  EFPAVPYSAW
2  RCNNVGVRIY  VDAVINHMCG  SGNSAGTHST  CGSYFNPNNR  EFSAVPYSAW
3  RCNNVGVRIY  VDAVINHMCG  SGAAAGTGTT  CGSYCNPGNR  EFPAVPYSAW
4  RCNNVGVRIY  VDAVINHMCG  NAVSAGTSST  CGSYFNPGSR  DFPAVPYSGW
5  RCSAAGVDIY  VDTLINHM..  .AAGSGTGTA  GNSF...GNK  SFPI..YSPQ 151                                                                200
1  DFNDNKCN..  .GEIDNYNDA  YQVRNCRLTG  LLDLALEKDY  VRTKVADYMN
2  YFNDNKCN..  .GEINNYNDA  NQVRNCRLSG  LLDLALDKDY  VRTKVADYMN
3  DFNDGKCKTA  SGGIESYNDP  YQVRDCQLVG  LLDLALEKDY  VRSMIADYLN
4  DFNDGKCKTG  SGDIENYNDA  TQVRDCRLTG  LLDLALEKDY  VRSKIAEYMN
5  DFHES.CTIN  NSDYG..NDR  YRVQNCELVG  LADLDTASNY  VQNTIAAYIN 201                                                                250
1  HLIDIGVAGF  RLDAAKHMWP  RDIKAVLDKL  HNLNTKWFSQ  GSRPFIFQEV
2  NLIDIGVAGF  RLDAAKHMWP  GDIKAVLDKL  HNLNTKWFSQ  GSRPFIFQEV
3  KLIDIGVAGF  RLDASKHMWP  GDIKAVLDKL  HNLNTNWFPA  GSRPFIFQEV
4  HLIDIGVAGF  RLDASKHMWP  GDIKAILDKL  HNLNSNWFPA  GSKPFIYQEV
5  DLQAIGVKGF  RFDASKHVAA  SDIQSLMAKV  N.........  .GSPVVFQEV 251                                                                300
1  IDLGGEAIKG  SEYFGNGRVT  EFKYGAKLGT  VIRKWNGEKM  SYLKNWGEGW
2  IDLGGEAIKG  SEYFGNGRVT  EFKYGAKLGT  VIRKWNGEKM  SYLKNWGEGW
3  IDLGGEAIKS  GEYFSNGRVT  EFKYGAKLGT  VVRKWSGEKM  SYLKNWGEGW
4  IDLGGEPIKS  SDYFGNGRVT  EFKYGAKLGT  VIRKWNGEKM  SYLKNWGEGW
5  IDQGGEAVGA  SEYLSTGLVT  EFKYSTELGN  TFR...NGSL  AWLSNFGEGW 301                                                                350
1  GLVPSDRALV  FVDNHDNQRG  HGAGGSSILT  FWDARMYKMA  VGFMLAHPYG
2  GFVPTDRALV  FVDNHDNQRG  HGAGGASILT  FWDARMYKMA  VGFMLAHPYG
3  GFMPSDRALV  FVDNHDNQRG  HGAGGSSILT  FWDAYRKLVA  VGFMLAHPYG
4  GFVPSDRALV  FVDNHDNQRG  HGAGGASILT  FWDARLYKMA  VGFMLAHPYG
5  GFMPSSSAVV  FVDNHDNQRG  HGGAG.NVIT  FEDGRLYDLA  NVFMLAYPYG 351                                                                400
1  FTRVMSSYRW  NRNFQNGKDQ  NDWIGPPNNN  GVTKEVTINA  DTTCGNDWVC
2  FTRVMSSYRR  TRNFQNGKDV  NDWIGPPNNN  GVTKEVTINP  DTTCGNDWVC
3  FTRVMSSYRW  ARNFVNGEDV  NDWIGPPNNN  GVIKEVTINA  DTTCGNDWVC
4  FTRVMSSYRW  PRQFQNGNDV  NDWVGPPNNN  GVIKEVTINP  DTTCGNDWVC
5  YPKVMSSY..  ..DFHGDTDA  GGPNVPVHNN  GNLE......  ..CFASNWKC
```

Fig. 4 (a)

```
      401                                                              450
1  EHRWRQIRNM  VAFRNVVNGQ  .PFSNWWDNN  SNQVAFSRGN  RGFIVFNNDD
2  EHRWRQIRNM  VAFRNVVNGQ  .PFANWWDNG  SNQVAFSRGN  RGFIVFNNDD
3  EHRWREIRNM  VWFRNVVDGE  .PFANWWDNG  SNQVAFGRGN  RGFIVFNNDD
4  EHRWRQIRNM  VIFRNVVDGQ  .PFTNWYDNG  SNQVAFGRGN  RGFIVFNNDD
5  EHRWSYIAGG  VDFRNNTADN  WAVTNWWDNT  NNQISFGRGS  SGHMAINKED 451                                                              500
1  WALSATLQTG  LPAGTYCDVI  SGDKVDG..N  CTGLRVNVGS  DGKAHFSISN
2  WALSSTLQTG  LPAGTYCDVI  SGDKVNG..N  CTGLKVNVGS  DGKAHFSISN
3  WQLSSTLQTG  LPAGTYCDVI  SGDKVGN..S  CTGIKVYVSS  DGKAQFSISN
4  WSFSLTLQTG  LPAGTYCDVI  SGDKING..N  CTGIKIYVSD  DGKAHFSISN
5  STLTATVQTD  MASGQYCNVL  KGELSADAKS  CSGEVITVNS  DGTINLNIGA 501             521
          1  SAEDPFIAIH  ADSKL..... .
          2  SAEDPFIAIH  ADSKL..... .
          3  SAEDPFIAIH  AESKL..... .
          4  SAEDPFIAIH  AESKL..... .
          5  WDA...MAIH  KNAKLNTSSA S
```

α-AMYLASE MUTANTS

CROSS-REFERENCE TO RELATED APPLICATIONS

This application is a divisional of U.S. Ser. No. 09/183,412 filed on Oct. 30, 1998, now U.S. Pat. No. 6,204,232 and claims priority under 35 U.S.C. 119 of Danish application no. 1240/97 filed on Oct. 30, 1997, Danish application no. PA 1998 00936 filed on Jul. 14, 1998, U.S. provisional application No. 60/064,662 filed on Nov. 6, 1997 and U.S. provisional application No. 60/093,234 filed on Jul. 17, 1998, the contents of which are fully incorporated herein by reference.

FIELD OF THE INVENTION

The present invention relates to variants (mutants) of parent Termamyl-like α-amylases with higher activity at medium temperatures and/or high pH.

BACKGROUND OF THE INVENTION

α-Amylases (α-1,4-glucan-4-glucanohydrolases, EC 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of α-amylases such as Termamyl-like α-amylases variants are known from e.g. WO 90/11352, WO 95/10603, WO 95/26397, WO 96/23873 and WO 96/23874.

Among more recent disclosures relating to α-amylases, WO 96/23874 provides three-dimensional, X-ray crystal structural data for a Termamyl-like α-amylase which consists of the 300 N-terminal amino acid residues of the B. amyloliquefaciens α-amylase (BAN™) and amino acids 301–483 of the C-terminal end of the B. licheniformis α-amylase comprising the amino acid sequence (the latter being available commercially under the tradename Termamyl™), and which is thus closely related to the industrially important Bacillus α-amylases (which in the present context are embraced within the meaning of the term "Termamyl-like α-amylases", and which include, inter alia, the B. licheniformis, B. amyloliquefaciens (BAN™) and B. stearothermophilus (BSG™) α-amylases). WO 96/23874 further describes methodology for designing, on the basis of an analysis of the structure of a parent Termamyl-like α-amylase, variants of the parent Termamyl-like α-amylase which exhibit altered properties relative to the parent.

BRIEF DISCLOSURE OF THE INVENTION

The present invention relates to novel α-amylolytic variants(mutants) of a Termamyl-like α-amylase which exhibit improved wash performance (relative to the parent α-amylase) at high pH and at a medium temperature.

The term "medium temperature" means in the context of the invention a temperature from 10° C. to 60° C. preferably 20° C. to 50° C., especially 30–40° C.

The term "high pH" means the alkaline pH which today are used for washing, more specifically from about pH 8 to 10.5.

In the context of the invention a "low temperature α-amylase" means an α-amylase which has an relative optimum activity in the temperature range from 0–30° C.

In the context of the invention a "medium temperature α-amylase" means an α-amylase which has an optimum activity in the temperature range from 30–60° C. For instance, SP690 and SP722 α-amaylases, respectively, are "medium temperature α-amylases.

In the context of the invention a "high temperature α-amylase" is an α-amylase having the optimum activity in the temperature range from 60–110° C. For instance, Termamyl is a "high temperature α-amylase.

Alterations in properties which may be achieved in variants(mutants) of the invention are alterations in: the stability of the Termamyl-like α-amylase at a pH from 8 to 10.5, and/or the $Ca^{2+}$ stability at pH 8 to 10.5, and/or the specific activity at temperatures from 10 to 60° C., preferably 20–50° C., especially 30–40° C.

It should be noted that the relative temperature optimum often is dependent on the specific pH used. In other words the relative temperature optimum determined at, e.g., pH 8 may be substantially different from the relative temperature optimum determined at, e.g., pH 10.

The temperature's influence on the enzymatic activity

The dynamics in the active site and surroundings are dependent on the temperature and the amino acid composition and of strong importance for the relative temperature optimum of an enzyme. By comparing the dynamics of medium and high temperature α-amylases, regions of importance for the function of high temperature α-amylases at medium temperatures can be determined. The temperature activity profile of the SP722 α-amaylase (SEQ ID NO: 2) and the B. licheniformis α-amylase (available from Novo Nordisk as Termamyl®) (SEQ ID NO: 4) are shown in FIG. 2.

The relative temperature optimum of SP722 in absolute activities are shown to be higher at medium range temperatures (30–60° C.) than the homologous B. licheniformis α-amylase, which have an optimum activity around 60–100° C. The profiles are mainly dependent on the temperature stability and the dynamics of the active site residues and their surroundings. Further, the activity profiles are dependent on the pH used and the pKa of the active site residues.

In the first aspect the invention relates to a variant of a parent Termamyl-like α-amylase, which variant has α-amylase activity, said variant comprises one or more mutations corresponding to the following mutations in the amino acid sequence shown in SEQ ID NO: 2:

T141, K142, F143, D144, F145, P146, G147, R148, G149, Q174, R181, G182, D183, G184, K185, A186, W189, S193, N195, H107, K108, G109, D166, W167, D168, Q169, S170, R171, Q172, F173, F267, W268, K269, N270, D271, L272, G273, A274, L275, K311, E346, K385, G456, N457, K458, P459, G460, T461, V462, T463.

A variant of the invention have one or more of the following substitutions or deletions:

T141A,D,R,N,C,E,Q,G,H,I,L,K,M,F,P,S,W,Y,V;
K142A,D,R,N,C,E,Q,G,H,I,L,M,F,P,S,T,W,Y,V;
F143A,D,R,N,C,E,Q,G,H,I,L,K,M,P,S,T,W,Y,V;
D144A,R,N,C,E,Q,G,H,I,L,K,M,F,P,S,T,W,Y,V;
F145A,D,R,N,C,E,Q,G,H,I,L,K,M,P,S,T,W,Y,V;
P146A,D,R,N,C,E,Q,G,H,I,L,K,M,F,S,T,W,Y,V;
G147A,D,R,N,C,E,Q,H,I,L,K,M,F,P,S,T,W,Y,V;
R148A,D,N,C,E,Q,G,H,I,L,K,M,F,P,S,T,W,Y,V;
G149A,D,R,N,C,E,Q,H,I,L,K,M,F,P,S,T,W,Y,V;
R181*,A,D,N,C,E,Q,G,H,I,L,K,M,F,P,S,T,W,Y,V;
G182*,A,D,R,N,C,E,Q,H,I,L,K,M,F,P,S,T,W,Y,V;
D183*,A,R,N,C,E,Q,G,H,I,L,K,M,F,P,S,T,W,Y,V;
G184*,A,R,D,N,C,E,Q,H,I,L,K,M,F,P,S,T,W,Y,V;
K185A,D,R,N,C,E,Q,G,H,I,L,M,F,P, S,T,W,Y,V;
A186D,R,N,C,E,Q,G,H,I,L,K,M,F,P,S,T,W,Y,V;
W189A,D,R,N,C,E,Q,G,H,I,L,K,M,F,P,S,T,Y,V;

S193A,D,R,N,C,E,Q,G,H,I,L,K,M,F,P,T,W,Y,V;
N195A,D,R,C,E,Q,G,H,I,L,K,M,F,P,S,T,W,Y,V;
H107A,D,R,N,C,E,Q,G,HI,L,K,M,F,P,S,T,W,Y,V;
K108A,D,R,N,C,E,Q,G,H,I,L,M,F,P,S,T,W,Y,V;
G109A,D,R,N,C,E,Q,G,H,I,L,K,M,F,P,S,T,W,Y,V;
D166A,R,N,C,E,Q,G,H,I,L,K,M,F,P,S,T,W,Y,V;
W167A,D,R,N,C,E,Q,G,H,I,L,K,M,F,P,S,T,Y,V;
D168A,R,N,C,E,Q,G,H,I,L,K,M,F,P,S,T,W,Y,V;
Q169A,D,R,N,C,E,G,H,I,L,K,M,F,P,S,T,W,Y,V;
S170A,D,R,N,C,E,Q,G,H,I,L,K,M,F,P,T,W,Y,V;
R171A,D,N,C,E,Q,G,H,I,L,K,M,F,P,S,T,W,Y,V;
Q172A,D,R,N,C,E,G,H,I,L,K,M,F,P,S,T,W,Y,V;
F173A,D,R,N,C,E,Q,G,H,I,L,K,M,P,S,T,W,Y,V;
Q174*,A,D,R,N,C,E,G,H,I,L,K,M,F,P,S,T,W,Y,V;
F267A,D,R,N,C,E,Q,G,H,I,L,K,M,P,S,T,W,Y,V;
W268A,D,R,N,C,E,Q,G,H,I,L,K,M,F,P,S,T,Y,V;
K269A,D,R,N,C,E,Q,G,H,I,L,M,F,P,S,T,W,Y,V;
N270A,D,R,C,E,Q,G,H,I,L,K,M,F,P,S,T,W,Y,V;
D271A,R,N,C,E,Q,G,H,I,L,K,M,F,P,S,T,W,Y,V;
L272A,D,R,N,C,E,Q,G,H,I,K,M,F,P,S,T,W,Y,V;
G273A,D,R,N,C,E,Q,H,I,L,K,M,F,P,S,T,W,Y,V;
A274D,R,N,C,E,Q,G,H,I,L,K,M,F,P,S,T,W,Y,V;
L275A,D,R,N,C,E,Q,G,H,I,K,M,F,P,S,T,W,Y,V;
K311A,D,R,N,C,E,Q,G,H,I,L,M,F,P,S,T,W,Y,V;
E346A,D,R,N,C,Q,G,H,I,K,L,M,F,P,S,T,W,Y,V;
K385A,D,R,N,C,E,Q,G,H,I,L,M,F,P,S,T,W,Y,V;
G456A,D,R,N,C,E,Q,H,I,L,K,M,F,P,S,T,W,Y,V;
N457A,D,R,C,E,Q,G,H,I,L,K,M,F,P,S,T,W,Y,V;
K458A,D,R,N,C,E,Q,G,H,I,L,M,F,P,S,T,W,Y,V;
P459A,D,R,N,C,E,Q,G,H,I,L,K,M,F,S,T,W,Y,V;
G460A,D,R,N,C,E,Q,H,I,L,K,M,F,P,S,T,W,Y,V;
T461A,D,R,N,C,E,Q,G,H,I,L,K,M,F,P,S,W,Y,V;
V462A,D,R,N,C,E,Q,G,H,I,L,K,M,F,P,S,T,W,Y;
T463A,D,R,N,C,E,Q,G,H,I,L,K,M,F,P,S,W,Y,V.

Preferred are variants having one or more of the following substitutions or deletions:

K142R; S193P; N195F; K269R,Q; N270Y,R,D; K311R; E346Q; K385R; K458R; P459T; T461P; Q174*; R181Q,N,S; G182T,S,N; D183*; G184*; K185A,R,D,C,E,Q,G,H,I,L,M,N,F,P,S,T,W,Y,V; A186T,S,N,I,V,R; W189T,S,N,Q.

Especially preferred are variants having a deletion in positions D183 and G184 and further one or more of the following substitutions or deletions:

K142R; S193P; N195F; K269R,Q; N270Y,R,D; K311R; E346Q; K385R; K458R; P459T; T461P; Q174*; R181Q,N,S; G182T,S,N; K185A,R,D,C,E,Q,G,H,I,L,M,N,F,P,S,T,W,Y,V; A186T,S,N,I,V,R; W189T,S,N,Q.

The variants of the invention mentioned above exhibits an alteration in at least one of the following properties relative to the parent $\alpha$-amylase:

i) improved pH stability at a pH from 8 to 10.5; and/or
ii) improved $Ca^{2+}$ stability at pH 8 to 10.5, and/or
iii) increased specific activity at temperatures from 10 to 60° C., preferably 20–50° C., especially 30–40° C. Further, details will be described below.

The invention further relates to DNA constructs encoding variants of the invention; to methods for preparing variants of the invention; and to the use of variants of the invention, alone or in combination with other enzymes, in various industrial products or processes, e.g., in detergents or for starch liquefaction.

In a final aspect the invention relates to a method of providing $\alpha$-amylases with altered pH optimum, and/or altered temperature otimum, and/or improved stability.

Nomenclature

In the present description and claims, the conventional one-letter and three-letter codes for amino acid residues are used. For ease of reference, $\alpha$-amylase variants of the invention are described by use of the following nomenclature:

Original amino acid(s):position(s):substituted amino acid (s)

According to this nomenclature, for instance the substitution of asparagine for alanine in position 30 is shown as:
ALa30Asn or A30N a deletion of alanine in the same position is shown as:
Ala30* or A30* and insertion of an additional amino acid residue, such as lysine, is shown as:
Ala30AlaLys or A30AK A deletion of a consecutive stretch of amino acid residues, such as amino acid residues 30–33, is indicated as (30–33)* or Δ(A30–N33).

Where a specific $\alpha$-amylase contains a "deletion" in comparison with other $\alpha$-amylases and an insertion is made in such a position this is indicated as:
*36Asp or *36D for insertion of an aspartic acid in position 36

Multiple mutations are separated by plus signs, i.e.:
Ala30Asp+Glu34Ser or A30N+E34S representing mutations in positions 30 and 34 substituting asparagine and serine for alanine and glutamic acid, respectively.

When one or more alternative amino acid residues may be inserted in a given position it is indicated as
A30N,E or
A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:
R,N,D,A,C,Q,E,G,H,I,L,K,M,F,P,S,T,W,Y,V.

BRIEF DESCRIPTION OF THE DRAWING

FIGS. 1a–1c are an alignment of the amino acid sequences of six parent Termamyl-like $\alpha$-amylases. The numbers on the extreme left designate the respective amino acid sequences as follows:

1: SEQ ID NO: 2
2: Kaoamyl
3: SEQ ID NO: 1
4: SEQ ID NO: 5
5: SEQ ID NO: 4
6: SEQ ID NO: 3.

Figure 2:
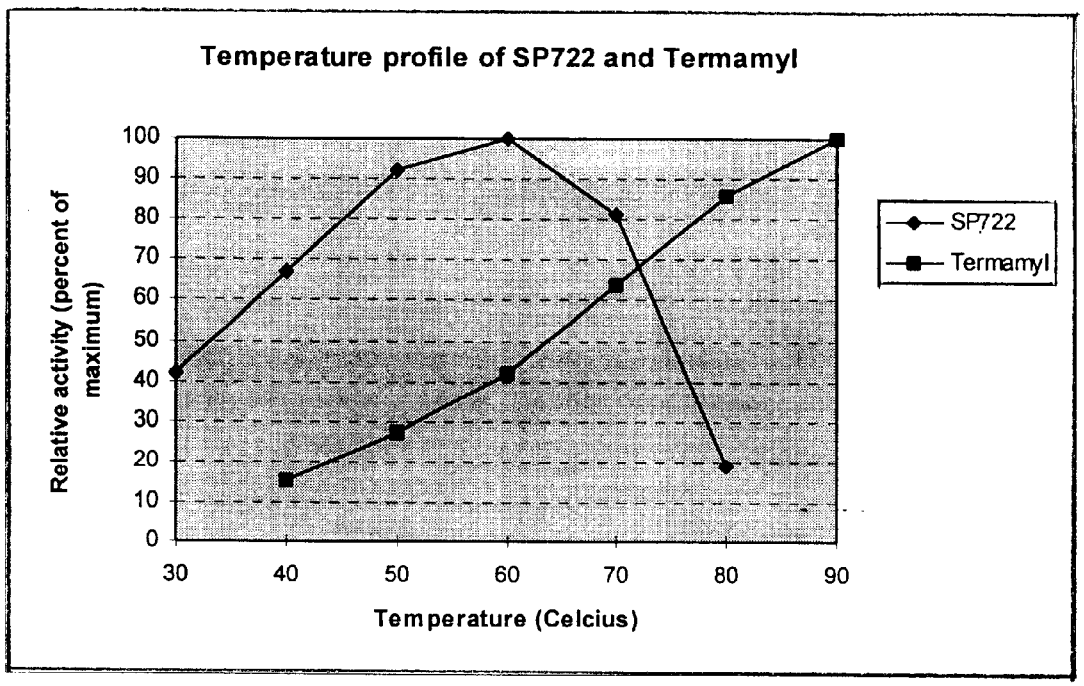

FIG. 2 shows the temperature activity profile of SP722 (SEQ ID NO: 2) (at pH 9) and B. licheniformis $\alpha$-amylase (SEQ ID NO: 4) (at pH 7.3).

Figure 3:
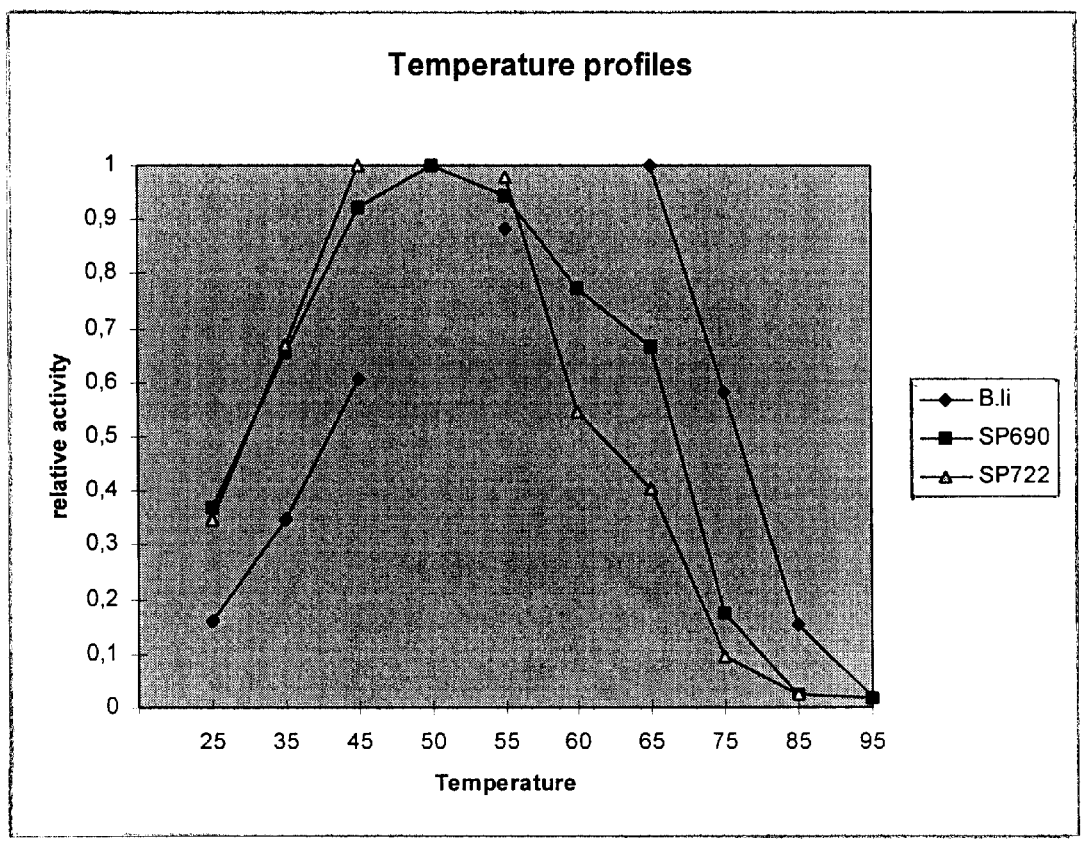

FIG. 3 shows the temperature profile for SP690 (SEQ ID NO: 1), SP722 (SEQ ID NO: 2), B. licheniformis $\alpha$-amylase (SEQ ID NO: 4) at pH 10.

FIGS. 4a–4b are an alignment of the amino acid sequences of five $\alpha$-amylases. The numbers on the extreme left designate the respective amino acid sequences as follows:

1: amyp_mouse
2: amyp_rat
3: amyp_pig porcine pancreatic alpha-amylase (PPA)
4: amyp_human
5: amy_altha A. haloplanctis alpha-amylase (AHA)

DETAILED DISCLOSURE OF THE INVENTION
The Termamyl-like $\alpha$-amylase

It is well known that a number of $\alpha$-amylases produced by Bacillus spp. are highly homologous on the amino acid level. For instance, the B. licheniformis $\alpha$-amylase comprising the amino acid sequence shown in SEQ ID NO:. 4 (commercially available as Termamyl™) has been found to be about 89% homologous with the B. amyloliquefaciens $\alpha$-amylase comprising the amino acid sequence shown in SEQ ID NO: 5 and about 79% homologous with the B. stearothermophilus $\alpha$-amylase comprising the amino acid sequence shown in SEQ ID NO: 3. Further homologous $\alpha$-amylases include an $\alpha$-amylase derived from a strain of the Bacillus sp. NCIB 12289, NCIB 12512, NCIB 12513 or DSM 9375, all of which are described in detail in WO 95/26397, and the $\alpha$-amylase described by Tsukamoto et al., *Biochemical and Biophysical Research Communications*, 151 (1988), pp. 25–31, (see SEQ ID NO: 6).

Still further homologous $\alpha$-amylases include the $\alpha$-amylase produced by the B. licheniformis strain described in EP 0252666 (ATCC 27811), and the $\alpha$-amylases identified in WO 91/00353 and WO 94/18314. Other commercial Termamyl-like B. licheniformis $\alpha$-amylases are comprised in the products Optitherm™ and Takatherm™ (available from Solvay), Maxamyl™ (available from Gist-brocades/Genencor), Spezym AA™ and Spezyme Delta AA™ (available from Genencor), and Keistase™ (available from Daiwa).

Because of the substantial homology found between these $\alpha$-amylases, they are considered to belong to the same class of $\alpha$-amylases, namely the class of "Termamyl-like $\alpha$-amylases".

Accordingly, in the present context, the term "Termamyl-like $\alpha$-amylase" is intended to indicate an $\alpha$-amylase which, at the amino acid level, exhibits a substantial homology to Termamyl™, i.e., the B. licheniformis $\alpha$-amylase having the amino acid sequence shown in SEQ ID NO:4 herein. In other words, all the following $\alpha$-amylases which has the amino acid sequences shown in SEQ ID NOS: 1, 2, 3, 4, 5, 6, 7 or 8 herein, or the amino acid sequence shown in SEQ ID NO: 1 of WO 95/26397 (the same as the amino acid sequence shown as SEQ ID NO: 7 herein) or in SEQ ID NO: 2 of WO 95/26397 (the same as the amino acid sequence shown as SEQ ID NO: 8 herein) or in Tsukamoto et al., 1988, (which amino acid sequence is shown in SEQ ID NO: 6 herein) are considered to be "Termamyl-like $\alpha$-amylase". Other Termamyl-like $\alpha$-amylases are $\alpha$-amylases i) which displays at least 60%, such as at least 70%, e.g., at least 75%, or at least 80%, e.g., at least 85%, at least 90% or at least 95% homology with at least one of said amino acid sequences shown in SEQ ID NOS: 1–8 and/or ii) displays immunological cross-reactivity with an antibody raised against at least one of said $\alpha$-amylases, and/or iii) is encoded by a DNA sequence which hybridizes to the DNA sequences encoding the above-specified $\alpha$-amylases which are apparent from SEQ ID NOS: 9, 10, 11, or 12 of the present application (which encoding sequences encode the amino acid sequences shown in SEQ ID NOS: 1, 2, 3, 4 and 5 herein, respectively), from SEQ ID NO: 4 of WO 95/26397 (which DNA sequence, together with the stop codon TAA, is shown in SEQ ID NO: 13 herein and encodes the amino acid sequence shown in SEQ ID NO: 8 herein) and from SEQ ID NO: 5 of WO 95/26397 (shown in SEQ ID NO: 14 herein), respectively.

In connection with property i), the "homology" may be determined by use of any conventional algorithm, preferably by use of the GAP progamme from the GCG package version 7.3 (June 1993) using default values for GAP penalties, which is a GAP creation penalty of 3.0 and GAP extension penalty of 0.1, (Genetic Computer Group (1991) Programme Manual for the GCG Package, version 7, 575 Science Drive, Madison, Wis., USA 53711).

A structural alignment between Termamyl (SEQ ID NO: 4) and a Termamyl-like $\alpha$-amylase may be used to identify equivalent/corresponding positions in other Termamyl-like $\alpha$-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149–155) and reverse threading (Huber, T ; Torda, AE, PROTEIN SCIENCE Vol. 7, No. 1 pp. 142–149 (1998).

Property ii) of the $\alpha$-amylase, i.e., the immunological cross reactivity, may be assayed using an antibody raised against, or reactive with, at least one epitope of the relevant Termamyl-like $\alpha$-amylase. The antibody, which may either be monoclonal or polyclonal, may be produced by methods known in the art, e.g., as described by Hudson et al., Practical Immunology, Third edition (1989), Blackwell Scientific Publications. The immunological cross-reactivity may be determined using assays known in the art, examples of which are Western Blotting or radial immunodiffusion assay, e.g., as described by Hudson et al., 1989. In this respect, immunological cross-reactivity between the $\alpha$-amylases having the amino acid sequences SEQ ID NOS: 1, 2, 3, 4, 5, 6, 7, or 8, respectively, has been found.

The oligonucleotide probe used in the characterisation of the Termamyl-like $\alpha$-amylase in accordance with property iii) above may suitably be prepared on the basis of the full or partial nucleotide or amino acid sequence of the $\alpha$-amylase in question.

Suitable conditions for testing hybridisation involve presoaking in 5xSSC and prehybridizing for 1 hour at $\approx$40° C. in a solution of 20% formamide, 5xDenhardt's solution, 50 mM sodium phosphate, pH 6.8, and 50 mg of denatured sonicated calf thymus DNA, followed by hybridisation in the same solution supplemented with 100 mM ATP for 18 hours at $\approx$40° C., followed by three times washing of the filter in 2xSSC, 0.2% SDS at 40° C. for 30 minutes (low stringency), preferred at 50° C. (medium stringency), more preferably at 65° C. (high stringency), even more preferably at $\approx$75$_0$C (very high stringency). More details about the hybridisation method can be found in Sambrook et al., Molecular_Cloning: A Laboratory Manual, 2nd Ed., Cold Spring Harbor, 1989.

In the present context, "derived from" is intended not only to indicate an $\alpha\alpha$-amylase produced or producible by a strain of the organism in question, but also an $\alpha$-amylase encoded by a DNA sequence isolated from such strain and produced in a host organism transformed with said DNA sequence. Finally, the term is intended to indicate an $\alpha$-amylase which is encoded by a DNA sequence of synthetic and/or cDNA origin and which has the identifying characteristics of the $\alpha$-amylase in question. The term is also intended to indicate that the parent $\alpha$-amylase may be a variant of a naturally occurring $\alpha$-amylase, i.e. a variant which is the result of a modification (insertion, substitution, deletion) of one or more amino acid residues of the naturally occurring $\alpha$-amylase.

Parent hybrid $\alpha$-amylases

The parent $\alpha$-amylase (i.e., backbone $\alpha$-amylase) may be a hybrid $\alpha$-amylase, i.e., an $\alpha$-amylase which comprises a combination of partial amino acid sequences derived from at least two $\alpha$-amylases.

The parent hybrid α-amylase may be one which on the basis of amino acid homology and/or immunological cross-reactivity and/or DNA hybridization (as defined above) can be determined to belong to the Termamyl-like α-amylase family. In this case, the hybrid α-amylase is typically composed of at least one part of a Termamyl-like α-amylase and part(s) of one or more other α-amylases selected from Termamyl-like α-amylases or non-Termamyl-like α-amylases of microbial (bacterial or fungal) and/or mammalian origin.

Thus, the parent hybrid α-amylase may comprise a combination of partial amino acid sequences deriving from at least two Termamyl-like α-amylases, or from at least one Termamyl-like and at least one non-Termamyl-like bacterial α-amylase, or from at least one Termamyl-like and at least one fungal α-amylase. The Termamyl-like α-amylase from which a partial amino acid sequence derives may, e.g., be any of those specific Termamyl-like α-amylase referred to herein.

For instance, the parent α-amylase may comprise a C-terminal part of an α-amylase derived from a strain of B. licheniformis, and a N-terminal part of an α-amylase derived from a strain of B. amyloliquefaciens or from a strain of B. stearothermophilus. For instance, the parent α-amylase may comprise at least 430 amino acid residues of the C-terminal part of the B. licheniformis α-amylase, and may, e.g., comprise a) an amino acid segment corresponding to the 37 N-terminal amino acid residues of the B. amyloliquefaciens α-amylase having the amino acid sequence shown in SEQ ID NO: 5 and an amino acid segment corresponding to the 445 C-terminal amino acid residues of the B. licheniformis α-amylase having the amino acid sequence shown in SEQ ID NO: 4, or a hybrid Termamyl-like α-amylase being identical to the Termamyl sequence, i.e., the Bacillus licheniformis α-amylase shown in SEQ ID NO: 4, except that the N-terminal 35 amino acid residues (of the mature protein) has been replaced by the N-terminal 33 residues of BAN (mature protein), i.e., the Bacillus amyloliquefaciens α-amylase shown in SEQ ID NO: 5; or b) an amino acid segment corresponding to the 68 N-terminal amino acid residues of the B. stearothermophilus α-amylase having the amino acid sequence shown in SEQ ID NO: 3 and an amino acid segment corresponding to the 415 C-terminal amino acid residues of the B. licheniformis α-amylase having the amino acid sequence shown in SEQ ID NO: 4.

Another suitable parent hybrid α-amylase is the one previously described in WO 96/23874 (from Novo Nordisk) constituting the N-terminus of BAN, Bacillus amyloliquefaciens α-amylase (amino acids 1–300 of the mature protein) and the C-terminus from Termamyl (amino acids 301–483 of the mature protein). Increased activity was achieved by substituting one or more of the following positions of the above hybrid α-amylase (BAN:1–300/Termamyl:301–483): Q360, F290, and N102. Particularly interesting substitutions are one or more of the following substitutions: Q360E,D; F290A,C,D,E,G,H,I,K,L,M,N,P,Q,R,S,T; N102D,E;

The corresponding positions in the SP722 α-amylase shown in SEQ ID NO: 2 are one or more of: S365, Y295, N106. Corresponding substitutions of particular interest in said α-amylase shown in SEQ ID NO: 2 are one or more of: S365D,E; Y295 A,C,D,E,G,H,I,K,L,M,N,P,Q,R,S,T; and N106D,E.

The corresponding positions in the SP690 α-amylase shown in SEQ ID NO: 1 are one or more of: S365, Y295, N106. The corresponding substitutions of particular interest are one or more of: S365D,E; Y295 A,C,D,E,G,H,I,K,L,M, N,P,Q,R,S,T; N106D,E.

The above mentioned non-Termamyl-like α-amylase may, e.g., be a fungal α-amylase, a mammalian or a plant α-amylase or a bacterial α-amylase (different from a Termamyl-like α-amylase). Specific examples of such α-amylases include the Aspergillus oryzae TAKA α-amylase, the A. niger acid α-amylase, the Bacillus subtilis α-amylase, the porcine pancreatic α-amylase and a barley α-amylase. All of these α-amylases have elucidated structures which are markedly different from the structure of a typical Termamyl-like α-amylase as referred to herein.

The fungal α-amylases mentioned above, i.e., derived from A. niger and A. oryzae, are highly homologous on the amino acid level and generally considered to belong to the same family of α-amylases. The fungal α-amylase derived from Aspergillus oryzae is commercially available under the tradename Fungamyl™.

Furthermore, when a particular variant of a Termamyl-like α-amylase (variant of the invention) is referred to—in a conventional manner—by reference to modification (e.g., deletion or substitution) of specific amino acid residues in the amino acid sequence of a specific Termamyl-like α-amylase, it is to be understood that variants of another Termamyl-like α-amylase modified in the equivalent position(s) (as determined from the best possible amino acid sequence alignment between the respective amino acid sequences) are encompassed thereby.

In a preferred embodiment of the invention the α-amylase backbone is derived from B. licheniformis (as the parent Termamyl-like α-amylase), e.g., one of those referred to above, such as the B. licheniformis α-amylase having the amino acid sequence shown in SEQ ID NO: 4.

Altered properties of variants of the invention

The following discusses the relationship between mutations which are present in variants of the invention, and desirable alterations in properties (relative to those a parent Termamyl-like α-amylase) which may result therefrom.

Improved stability at pH 8–10.5

In the context of the present invention, mutations (including amino acid substitutions) of importance with respect to achieving improved stability at high pH (i.e., pH 8–10.5) include mutations corresponding to mutations in one or more of the following positions in SP722 α-amylase (having the amino acid sequence shown in SEQ ID NO: 2): T141, K142, F143, D144, F145, P146, G147, R148, G149, R181, A186, S193, N195, K269, N270, K311, K458, P459, T461.

The variant of the invention have one or more of the following substitutions (using the SEQ ID NO: 2 numbering):

T141A,D,R,N,C,E,Q,G,H,I,L,K,M,F,P,S,W,Y,V;
K142A,D,R,N,C,E,Q,G,H,I,L,M,F,P,S,T,W,Y,V;
F143A,D,R,N,C,E,Q,G,H,I,L,K,M,P,S,T,W,Y,V;
D144A,R,N,C,E,Q,G,H,I,L,K,M,F,P,S,T,W,Y,V;
F145A,D,R,N,C,E,Q,G,H,I,L,K,M,P,S,T,W,Y,V;
P146A,D,R,N,C,E,Q,G,H,I,L,K,M,F,S,T,W,Y,V;
G147A,D,R,N,C,E,Q,H,I,L,K,M,F,P,S,T,W,Y,V;
R148A,D,N,C,E,Q,G,H,I,L,K,M,F,P,S,T,W,Y,V;
G149A,D,R,N,C,E,Q,H,I,L,K,M,F,P,S,T,W,Y,V;
K181A,D,R,N,C,E,Q,G,H,I,L,M,F,P,S,T,W,Y,V;
A186D,R,N,C,E,Q,G,H,I,L,P,K,M,F,S,T,W,Y,V;
S193A,D,R,N,C,E,Q,G,H,I,L,K,M,F,P,T,W,Y,V;
N195A,D,R,C,E,Q,G,H,I,L,K,M,F,P,S,T,W,Y,V;
K269A,D,R,N,C,E,Q,G,H,I,L,M,F,P,S,T,W,Y,V;
N270A,D,R,C,E,Q,G,H,I,L,K,M,F,P,S,T,W,Y,V;
K311A,D,R,N,C,E,Q,G,H,I,L,M,F,P,S,T,W,Y,V;
K458A,D,R,N,C,E,Q,G,H,I,L,M,F,P,S,T,W,Y,V;
P459A,D,R,N,C,E,Q,G,H,I,L,K,M,F,S,T,W,Y,V;

T461A,D,R,N,C,E,Q,G,H,I,L,K,M,F,P,S,W,Y,V.

Preferred high pH stability variants include one or more of the following substitutions in the SP722 α-amylase (having the amino acid sequence shown in SEQ ID NO: 2): K142R, R181S, A186T, S193P, N195F, K269R, N270Y, K311R, K458R, P459T and T461P.

In specific embodiments the Bacillus strain NCIB 12512 α-amylase having the sequence shown in SEQ ID NO: 1, or the B. stearothermophilus α-amylase having the sequence shown in SEQ ID NO: 3, or the B. licheniformis α-amylase having the sequence shown in SEQ ID NO: 4, or the B. amyloliquefaciens α-amylase having the sequence shown in SEQ ID NO: 5 is used as the backbone, i.e., parent Termamyl-like α-amylase, for these mutations.

As can been seen from the alignment in FIG. 1 the B. stearothermophilus α-amylase already has a Tyrosine at position corresponding to N270 in SP722. Further, the Bacillus strain NCIB 12512 α-amylase, the B. stearothermophilus α-amylase, the B. licheniformis α-amylase and the B. amyloliquefaciens α-amylase already have Arginine at position corresponding to K458 in SP722. Furthermore, the B. licheniformis α-amylase already has a Proline at position corresponding to T461 in SP722. Therefore, for said α-amylases these substitutions are not relevant.

α-amylase variants with improved stability at high pH can be constructed by making substitutions in the regions found using the molecular dynamics simulation mentioned in Example 2. The simulation depicts the region(s) that has a higher flexibility or mobility at high pH (i.e., pH 8–10.5) when compared to medium pH.

By using the structure of any bacterial alpha-amylase with homology (as defined below) to the Termamyl-like α-amylase (BA2), of which the 3D structure is disclosed in Appendix 1 of WO 96/23874 (from Novo Nordisk), it is possible to modelbuild the structure of such alpha-amylase and to subject it to molecular dynamics simulations. The homology of said bacterial α-amylase may be at least 60%, preferably be more than 70%, more preferably more than 80%, most preferably more than 90% homologous to the above mentioned Termamyl-like α-amylase (BA2), measured using the UWGCG GAP program from the GCG package version 7.3 (June 1993) using default values for GAP penalties [Genetic Computer Group (1991) Programme Manual for the GCG Package, version 7, 575 Science Drive, Madison, Wis., USA 53711]. Substitution of the unfavorable residue for another would be applicable.

Improved $Ca^{2+}$ stability at pH 8–10.5

Improved $Ca^{2+}$ stability means the stability of the enzyme under $Ca^{2+}$ depletion has been improved. In the context of the present invention, mutations (including amino acid substitutions) of importance with respect to achieving improved $Ca^{2+}$ stability at high pH include mutation or deletion in one or more positions corresponding to the following positions in the SP722 α-amylase having the amino acid sequence shown in SEQ ID NO: 2: R181, G182, D183, G184, K185, A186, W189, N195, N270, E346, K385, K458, P459.

A variant of the invention have one or more of the following substitutions or deletions:
R181*,A,D,N,C,E,Q,G,H,I,L,K,M,F,P,S,T,W,Y,V;
G182*,A,D,R,N,C,E,Q,H,I,L,K,M,F,P,S,T,W,Y,V;
D183*,A,R,N,C,E,Q,G,H,I,L,K,M,F,P,S,T,W,Y,V;
G184*,A,R,D,N,C,E,Q,H,I,L,K,M,F,P,S,T,W,Y,V;
K185A,D,R,N,C,E,Q,G,H,I,L,M,F,P,S,T,W,Y,V;
A186D,R,N,C,E,Q,G,H,I,L,K,M,F,P,S,T,W,Y,V;
W189A,D,R,N,C,E,Q,G,H,I,L,K,M,F,P,S,T,Y,V;
N195A,D,R,C,E,Q,G,H,I,L,K,M,F,P,S,T,W,Y,V;
N270A,R,D,N,C,E,Q,H,I,L,K,M,F,P,S,T,W,Y,V;
E346A,R,D,N,C,Q,G,H,I,L,K,M,F,P,S,T,W,Y,V;
K385A,R,D,N,C,E,Q,G,H,I,L,M,F,P,S,T,W,Y,V;
K458A,R,D,N,C,E,Q,G,H,I,L,M,F,P,S,T,W,Y,V;
P459A,R,D,N,C,E,Q,G,H,I,L,K,M,F,S,T,W,Y,V.

Preferred are variants having one or more of the following substitutions or deletions:
R181Q,N; G182T,S,N; D183*; G184*;
K185A,R,D,C,E,Q,G,H,I,L,M,N,F,P,S,T,W,Y,V; A186T, S,N,I,V;
W189T,S,N,Q; N195F, N270R,D; E346Q; K385R; K458R; P459T.

In specific embodiments the Bacillus strain NCIB 12512 α-amylase having the sequence shown in SEQ ID NO: 1, or the B. amyloliquefaciens α-amylase having the sequence shown in SEQ ID NO: 5, or the B. licheniformis α-amylase having the sequence shown in SEQ ID NO: 4 are used as the backbone for these mutations.

As can been seen from the alignment in FIG. 1 the B. licheniformis α-amylase does not have the positions corresponding to D183 and G184 in SP722. Therefore for said α-amylases these deletions are not relevant.

In a preferred embodiment the variant is the Bacillus strain NCIB 12512 α-amylase with deletions in D183 and G184 and further one of the following substitutions: R181Q,N and/or G182T,S,N and/or D183*; G184* and/or K185A,R,D,C,E,Q,G,H,I,L,M,N,F,P,S,T,W,Y,V and/or A186T,S,N,I,V and/or W189T,S,N,Q and/or N195F and/or N270R,D and/or E346Q and/or K385R and/or K458R and/or P459T.

Increased specific activity at medium temperature

In a further aspect of the present invention, important mutations with respect to obtaining variants exhibiting increased specific activity at temperatures from 10–60° C., preferably 20–50° C., especially 30–40° C., include mutations corresponding to one or more of the following positions in the SP722 α-amylase having the amino acid sequence shown in SEQ ID NO: 2:

H107, K108, G109, D166, W167, D168, Q169, S170, R171, Q172, F173, Q174, D183, G184, N195, F267, W268, K269, N270, D271, L272, G273, A274, L275, G456, N457, K458, P459, G460, T461, V462, T463.

The variant of the invention have one or more of the following substitutions:
H107A,D,R,N,C,E,Q,G,I,L,K,M,F,P,S,T,W,Y,V;
K108A,D,R,N,C,E,Q,G,H,I,L,M,F,P,S,T,W,Y,V;
G109A,D,R,N,C,E,Q,H,I,L,K,M,F,P,S,T,W,Y,V;
D166A,R,N,C,E,Q,G,H,I,L,K,M,F,P,S,T,W,Y,V;
W167A,D,R,N,C,E,Q,G,H,I,L,K,M,F,P,S,T,Y,V;
D168A,R,N,C,E,Q,G,H,I,L,K,M,F,P,S,T,W,Y,V;
Q169A,D,R,N,C,E,G,H,I,L,K,M,F,P,S,T,W,Y,V;
S170A,D,R,N,C,E,Q,G,H,I,L,K,M,F,P,T,W,Y,V;
R171A,D,N,C,E,Q,G,H,I,L,K,M,F,P,S,T,W,Y,V;
Q172A,D,R,N,C,E,G,H,I,L,K,M,F,P,S,T,W,Y,V;
F173A,D,R,N,C,E,Q,G,H,I,L,K,M,P,S,T,W,Y,V;
Q174*,A,D,R,N,C,E,G,H,I,L,K,M,F,P,S,T,W,Y,V;
D183*,A,D,R,N,C,E,Q,G,H,I,L,K,M,F,P,S,W,Y,V;
G184*,A,R,N,C,E,Q,G,H,I,L,K,M,F,P,S,T,W,Y,V;
N195A,D,R,C,E,Q,G,H,I,L,K,M,F,P,S,T,W,Y,V;
F267A,D,R,N,C,E,Q,G,H,I,L,K,M,P,S,T,W,Y,V;
W268A,D,R,N,C,E,Q,G,H,I,L,K,M,F,P,S,T,Y,V;
K269A,D,R,N,C,E,Q,G,H,I,L,M,F,P,S,T,W,Y,V;
N270A,D,R,C,E,Q,G,H,I,L,K,M,F,P,S,T,W,Y,V;
D271A,R,N,C,E,Q,G,H,I,L,K,M,F,P,S,T,W,Y,V;
L272A,D,R,N,C,E,Q,G,H,I,K,M,F,P,S,T,W,Y,V;
G273A,D,R,N,C,E,Q,H,I,L,K,M,F,P,S,T,W,Y,V;
A274D,R,N,C,E,Q,G,H,I,L,K,M,F,P,S,T,W,Y,V;

L275A,D,R,N,C,E,Q,G,H,I,K,M,F,P,S,T,W,Y,V;
G456A,D,R,N,C,E,Q,H,I,L,K,M,F,P,S,T,W,Y,V;
N457A,D,R,C,E,Q,G,H,I,L,K,M,F,P,S,T,W,Y,V;
K458A,D,R,N,C,E,Q,G,H,I,L,M,F,P,S,T,W,Y,V;
P459A,D,R,N,C,E,Q,G,H,I,L,M,F,S,T,W,Y,V;
G460A,D,R,N,C,E,Q,H,I,L,K,M,F,P,S,T,W,Y,V;
T461A,D,R,N,C,E,Q,G,H,I,L,K,M,F,P,S,W,Y,V;
V462A,D,R,N,C,E,Q,G,H,I,L,K,M,F,P,S,T,W,Y;
T463A,D,R,N,C,E,Q,G,H,I,L,K,M,F,P,S,W,Y,V.

Preferred variants has one or more of the following substitutions or deletions: Q174*, D183*, G184*, K269S.

In a specific embodiment the B. licheniformis $\alpha$-amylase having the sequence shown in SEQ ID NO: 4 is used as the backbone for these mutations.

General mutations in variants of the invention: increased specific activity at medium temperatures The particularly interesting amino acid substitution are those that increase the mobility around the active site of the enzyme. This is accomplished by changes that disrupt stabilizing interaction in the vicinity of the active site, i.e., within preferably 10Å or 8Å or 6Å or 4Å from any of the residues constituting the active site.

Examples are mutations that reduce the size of side chains, such as
Ala to Gly,
Val to Ala or Gly,
Ile or Leu to Val, Ala, or Gly
Thr to Ser Such mutations are expected to cause increased flexibility in the active site region either by the introduction of cavities or by the structural rearrangements that fill the space left by the mutation.

It may be preferred that a variant of the invention comprises one or more modifications in addition to those outlined above. Thus, it may be advantageous that one or more Proline residues present in the part of the $\alpha$-amylase variant which is modified is/are replaced with a non-Proline residue which may be any of the possible, naturally occurring non-Proline residues, and which preferably is an Alanine, Glycine, Serine, Threonine, Valine or Leucine.

Analogously, it may be preferred that one or more Cysteine residues present among the amino acid residues with which the parent $\alpha$-amylase is modified is/are replaced with a non-Cysteine residue such as Serine, Alanine, Threonine, Glycine, Valine or Leucine.

Furthermore, a variant of the invention may—either as the only modification or in combination with any of the above outlined modifications—be modified so that one or more Asp and/or Glu present in an amino acid fragment corresponding to the amino acid fragment 185–209 of SEQ ID NO: 4 is replaced by an Asn and/or Gln, respectively. Also of interest is the replacement, in the Termamyl-like $\alpha$-amylase, of one or more of the Lys residues present in an amino acid fragment corresponding to the amino acid fragment 185–209 of SEQ ID NO: 4 by an Arg.

It will be understood that the present invention encompasses variants incorporating two or more of the above outlined modifications.

Furthermore, it may be advantageous to introduce point-mutations in any of the variants described herein.

$\alpha$-amylase variants having increased mobility around the active site:

The mobility of $\alpha$-amylase variants of the invention may be increased by replacing one or more amino acid residue at one or more positions close to the substrate site. These positions are (using the SP722 $\alpha$-amylase (SEQ ID NO: 2) numbering) : V56, K108, D168, Q169, Q172, L201, K269, L272, L275, K446, P459.

Therefore, in an aspect the invention relates to variants being mutated in one or more of the above mentioned positions.

Preferred substitutions are one or more of the following:
V56A,G,S,T;
K108A,D,E,Q,G,H,I,L,M,N,S,T,V;
D168A,G,I,V,N,S,T;
Q169A,D,G,H,I,L,M,N,S,T,V;
Q172A,D,G,H,I,L,M,N,S,T,V;
L201A,G,I,V,S,T;
K269A,D,E,Q,G,H,I,L,M,N,S,T,V;
L272A,G,I,V,S,T;
L275A,G,I,V,S,T;
Y295A,D,E,Q,G,H,I,L,M,N,F,S,T,V;
K446A,D,E,Q,G,H,I,L,M,N,S,T,V;
P459A,G,I,L,S,T,V.

In specific embodiments of the invention the Bacillus strain NCIB 12512 $\alpha$-amylase having the sequence shown in SEQ ID NO: 1, or the B. stearothermophilus $\alpha$-amylase having the sequence shown in SEQ ID NO: 3, or the B. licheniformis $\alpha$-amylase having the sequence shown in SEQ ID NO: 4, or the B. amyloliquefaciens $\alpha$-amylase having the sequence shown in SEQ ID NO: 5 are used as the backbone for these mutations.

As can been seen from the alignment in FIG. 1 the B. licheniformis $\alpha$-amylase and the B. amyloliquefaciens $\alpha$-amylase have a Glutamine at position corresponding to K269 in SP722. Further, the B. stearothermophilus $\alpha$-amylase has a Serine at position corresponding to K269 in SP722. Therefore, for said $\alpha$-amylases these substitutions are not relevant.

Furthermore, as can been seen from the alignment in FIG. 1 the B. amyloliquefaciens $\alpha$-amylase has an Alanine at position corresponding to L272 in SP722, and the B. stearothermophilus $\alpha$-amylase has a Isoleucine at the position corresponding to L272 in SP722. Therefore, for said $\alpha$-amylases these substitutions are not relevant.

As can been seen from the alignment in FIG. 1, the Bacillus strain 12512 $\alpha$-amylase has a Isoleucine at position corresponding to L275 in SP722. Therefore for said $\alpha$-amylase this substitution is not relevant.

As can been seen from the alignment in FIG. 1 the B. amyloliquefaciens $\alpha$-amylase has a Phenylalanine at position corresponding to Y295 in SP722. Further, the B. stearothermophilus $\alpha$-amylase has an Asparagine at position corresponding to Y295 in SP722. Therefore, for said $\alpha$-amylases these substitutions are not relevant.

As can been seen from the alignment in FIG. 1 the B. licheniformis $\alpha$-amylase and the B. amyloliquefaciens $\alpha$-amylase have a Asparagine at position corresponding to K446 in SP722. Further, the B. stearothermophilus $\alpha$-amylase has a Histidine at position corresponding to K446 in SP722. Therefore, for said $\alpha$-amylases these substitutions are not relevant.

As can been seen from the alignment in FIG. 1 the B. licheniformis $\alpha$-amylase, the B. amyloliquefaciens $\alpha$-amylase and the B. stearothermophilus $\alpha$-amylase have a Serine at position corresponding to P459 in SP722. Further, the Bacillus strain 12512 $\alpha$-amylase has a Threonine at position corresponding to P459 in SP722. Therefore, for said $\alpha$-amylases these substitutions are not relevant.

Stabilization of enzymes having high activity at medium temperatures

In a further embodiment the invention relates to improving the stability of low temperature $\alpha$-amylases (e.g, Alteromonas haloplanctis (Feller et al., (1994), Eur. J. Biochem 222:441–447), and medium temperature $\alpha$-amylases (e.g., SP722 and SP690) possessing medium temperature activity, i.e., commonly known as psychrophilic enzymes and mesophilic enzymes. The stability can for this particular enzyme class be understood either as thermostability or the stability at Calcium depletion conditions.

Typically, enzymes displaying the high activity at medium temperatures also display severe problems under conditions that stress the enzyme, such as temperature or Calcium depletion.

Consequently, the objective is to provide enzymes that at the same time display the desired high activity at medium temperatures without loosing their activity under slightly stressed conditions.

The activity of the stabilized variant measured at medium temperatures should preferably be between 100% or more and 50%, and more preferably between 100% or more and 70%, and most preferably between 100% or more and 85% of the original activity at that specific temperature before stabilization of the enzyme and the resulting enzyme should withstand longer incubation at stressed condition than the wild type enzyme.

Contemplated enzymes include $\alpha$-amylases of, e.g., bacterial or fungal origin.

An example of such a low temerature $\alpha$-amylase is the one isolated from *Alteromonas haloplanctis* (Feller et al., (1994), Eur. J. Biochem 222:441–447). The crystal structure of this alph $\alpha$-amylase has been solved (Aghajari et al., (1998), Protein Science 7:564–572).

The *A. haloplanctis* alpha-amylase (5 in alignment shown in FIG. 4) has a homology of approximately 66% to porcine pancreatic alpha-amylase (PPA) (3 in the alignment shown in FIG. 4). The PPA 3D structure is known, and can be obtained from Brookhaven database under the name 1OSE or 1DHK. Based on the homology to other more stable alpha amylases, stabilization of "the low temperature highly active enzyme" from *Alteromonas haloplanctis* alpha-amylase, can be obtained and at the same time retaining the desired high activity at medium temperatures.

FIG. 4 shown a multiple sequence alignments of five $\alpha$-amylases, including the AHA and the PPA $\alpha$-amylase. Specific mutations giving increased stability in *Alteromonas haloplantis* alpha-amylase:

T66P, Q69P, R155P, Q177R, A205P, A232P, L243R, V295P, S315R.

Methods for preparing $\alpha$-amylase variants

Several methods for introducing mutations into genes are known in the art. After a brief discussion of the cloning of $\alpha$-amylase-encoding DNA sequences, methods for generating mutations at specific sites within the $\alpha$-amylase-encoding sequence will be discussed.

Cloning a DNA sequence encoding an $\alpha$-amylaseCloning a DNA sequence encoding an $\alpha$-amylaseCloning a DNA sequence encoding an $\alpha$-amylaseCloning a DNA sequence encoding an a-amylase The DNA sequence encoding a parent $\alpha$-amylase may be isolated from any cell or microorganism producing the $\alpha$-amylase in question, using various methods well known in the art. First, a genomic DNA and/or cDNA library should be constructed using chromosomal DNA or messenger RNA from the organism that produces the $\alpha$-amylase to be studied. Then, if the amino acid sequence of the $\alpha$-amylase is known, homologous, labeled oligonucleotide probes may be synthesized and used to identify $\alpha$-amylase-encoding clones from a genomic library prepared from the organism in question. Alternatively, a labeled oligonucleotide probe containing sequences homologous to a known $\alpha$-amylase gene could be used as a probe to identify $\alpha$-amylase-encoding clones, using hybridization and washing conditions of lower stringency.

Yet another method for identifying $\alpha$-amylase-encoding clones would involve inserting fragments of genomic DNA into an expression vector, such as a plasmid, transforming $\alpha$-amylase-negative bacteria with the resulting genomic DNA library, and then plating the transformed bacteria onto agar containing a substrate for $\alpha$-amylase, thereby allowing clones expressing the $\alpha$-amylase to be identified.

Alternatively, the DNA sequence encoding the enzyme may be prepared synthetically by established standard methods, e.g., the phosphoroamidite method described by S. L. Beaucage and M. H. Caruthers (1981) or the method described by Matthes et al. (1984). In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Expression of $\alpha$-amylase variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an $\alpha$-amylase variant of the invention may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosomets) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an $\alpha$-amylase variant of the invention, especially in a bacterial host, are the promoter of the lac operon of *E.coli*, the *Streptomyces coelicolor* agarase gene dagA promoters, the promoters of the *Bacillus licheniformis* $\alpha$-amylase gene (amyL), the promoters of the *Bacillus stearothermophilus* maltogenic amylase gene (amyM), the promoters of the *Bacillus amyloliquefaciens* $\alpha$-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral $\alpha$-amylase, *A. niger* acid stable $\alpha$-amylase, *A. niger* glu-coamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the $\alpha$-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argb, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the Bacillus $\alpha$-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an $\alpha$-amylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual*, 2nd Ed., Cold Spring Harbor, 1989).

The cell of the invention, either comprising a DNA construct or an expression vector of the invention as defined above, is advantageously used as a host cell in the recombinant production of an $\alpha$-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gramnegative bacteria such as *E.coli.* The transformation of the bacteria may, for instance, be effected by protoplast transformation or by using competent cells in a manner known per se.

The yeast organism may favorably be selected from a species of Saccharomyces or Schizosaccharomyces, e.g. Saccharomyces cerevisiae. The filamentous fungus may advantageously belong to a species of Aspergillus, e.g., *Aspergillus oryzae* or *Aspergillus niger.* Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing an $\alpha$-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the $\alpha$-amylase variant of the invention. Suitable media are available from commercial suppliers or may be prepared according to published recipes (e.g. as described in catalogues of the American Type Culture Collection).

The $\alpha$-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The $\alpha$-amylase variants of this invention possesses valuable properties allowing for a variety of industrial applications. In particular, enzyme variants of the invention are applicable as a component in washing, dishwashing and hard-surface cleaning detergent compositions.

Numerous variants are particularly useful in the production of sweeteners and ethanol from starch, and/or for textile desizing. Conditions for conventional starch- conversion processes, including starch liquefaction and/or saccharification processes, are described in, e.g., U.S. Pat. No. 3,912,590 and in EP patent publications Nos. 252,730 and 63,909.

Detergent compositions

As mentioned above, variants of the invention may suitably be incorporated in detergent compositions. Reference is made, for example, to WO 96/23874 and WO 97/07202 for further details concerning relevant ingredients of detergent compositions (such as laundry or dishwashing detergents), appropriate methods of formulating the variants in such detergent compositions, and for examples of relevant types of detergent compositions.

Detergent compositions comprising a variant of the invention may additionally comprise one or more other enzymes, such as a lipase, cutinase, protease, cellulase, peroxidase or laccase, and/or another $\alpha$-amylase.

$\alpha$-amylase variants of the invention may be incorporated in detergents at conventionally employed concentrations. It is at present contemplated that a variant of the invention may be incorporated in an amount corresponding to 0.00001–1 mg (calculated as pure, active enzyme protein) of $\alpha$-amylase per liter of wash/dishwash liquor using conventional dosing levels of detergent.

The invention also relates to a method of providing $\alpha$-amylases with 1) altered pH optimum, and/or 2) altered temperature optimum, and/or 3) improved stability, comprising the following steps:

i) identifying (a) target position(s) and/or region(s) for mutation of the $_\alpha$-amylase by comparing the molecular dynamics of two or more $_\alpha$-amylase 3D structures having substantially different pH, temperature and/or stability profiles, ii) substituting, adding and/or deleting one or more amino acids in the identified position(s) and/or region(s).

In embodiment of the invention a medium temperature $_\alpha$-amylase is compared with a high temperature $_\alpha$-amylase. In another embodiment a low temperature $_\alpha$-amylase is compared with either a medium or a high temperature $_\alpha$-amylase.

The $_\alpha$-amylases compared should preferably be at least 70%, preferably 80%, up to 90%, such as up to 95%, especially 95% homologous with each other.

The $_\alpha$-amylases compared may be Termamyl-like $_\alpha$-amylases as defined above. In specific embodiment the $_\alpha$-amylases compared are the $_\alpha$-amylases shown in SEQ ID NO: 1 to SEQ ID NO: 8.

In another embodiment the stability profile of the $_\alpha$-amylases in question compared are the $Ca^{2+}$ dependency profile.

MATERIALS AND METHODS

Enzymes:
SP722: (SEQ ID NO: 2, available from Novo Nordisk)
Termamyl™ (SEQ ID NO: 4, available from Novo Nordisk)
SP690: (SEQ ID NO: 1, available from Novo Nordisk)
Bacillus subtilis SHA273: see WO 95/10603
Plasmids
pJE1 contains the gene encoding a variant of SP722 $_\alpha$-amylase (SEQ ID NO: 2): viz. deletion of 6 nucleotides corresponding to amino acids D183–G184 in the mature protein. Transcription of the JE1 gene is directed from the amyL promoter. The plasmid further more contains the origin of replication and cat-gene conferring resistance towards kanamycin obtained from plasmid pUB110 (Gryczan, TJ et al. (1978), J. Bact. 134:318–329).
Methods:
Construction of library vector pDorK101

The E. coli/Bacillus shuttle vector pDorK101 (described below) can be used to introduce mutations without expression of $_\alpha$-amylase in E. coli and then be modified in such way that the $_\alpha$-amylase is active in Bacillus. The vector was constructed as follows: The JE1 encoding gene (SP722 with the deletion of D183–G184) was inactivated in pJE1 by gene interruption in the PstI site in the 5'coding region of the SEQ ID NO: 2: SP722 by a 1.2 kb fragment containing an E. coli origin of replication. This fragment was PCR amplified from the pUC19 (GenBank Accession #:X02514) using the forward primer: 5'-gacctgcagtcaggcaacta-3' and the reverse primer: 5'-tagagtcgacctgcaggcat-3'. The PCR amplicon and the pJE1 vector were digested with PstI at 37° C. for 2 hours. The pJE1 vector fragment and the PCR fragment were ligated at room temperature. for 1 hour and transformed in E. coli by electrotransformation. The resulting vector is designated pDorK101.
Filter screening assays The assay can be used to screening of Termamyl-like $_\alpha$-amylase variants having an improved stability at high pH compared to the parent enzyme and Termamyl-like $_\alpha$-amylase variants having an improved stability at high pH and medium temperatures compared to the parent enzyme depending of the screening temperature setting High pH filter assay Bacillus libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with 10 μg/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6–10.6 and incubated at room temperature(can be altered from 10–60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6–10.6. The assay plates with nitrocellulose filters are marked the same way as the filter sandwich and incubated for 2 hours. at room temperature. After removal of the filters the assay plates are stained with 10% Lugol solution. Starch degrading variants are detected as white spots on dark blue background and then identified on the storage plates. Positive variants are rescreened twice under the same conditions as the first screen.

Low calcium filter assay

The Bacillus library are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with a relevant antibiotic, e.g., kanamycin or chloramphenicol, at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with carbonate/bicarbonate buffer pH 8.5–10 and with different EDTA concentrations (0.001 mM -100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5–10. The assay plates with nitrocellulose filters are marked the same way as the filter sandwich and incubated for 2 hours. at room temperature. After removal of the filters the assay plates are stained with 10% Lugol solution. Starch degrading variants are detected as white spots on dark blue background and then identified on the storage plates. Positive variants are rescreened twice under the same conditions as the first screen.

Method to obtaining the regions of interest:

There are three known 3D structures of bacterial $_\alpha$-amylases. Two of B. licheniformis $_\alpha$-amylase, Brookhaven database 1BPL (Machius et al. (1995), J. Mol. Biol. 246, p. 545–559) and 1VJS (Song et al. (1996), Enzymes for Carbohydrate 163 Engineering (Prog. Biotechnol. V 12). These two structures are lacking an important piece of the structure from the so-called B-domain, in the area around the two Calcium ions and one Sodium ion binding sites. We have therefore used a 3D structure of an $_\alpha$-amylase BA2 (WO 96/23874 which are a hybrid between BAN™ (SEQ ID NO: 5) and B. licheniformis $_\alpha$-amylase (SEQ ID NO: 4). On basis of the structure a model of B. licheniformis alpha amylase and the SP722 $_\alpha$-amylase has been build.

Fermentation and purification of α-amylase variants

Fermentation and purification may be performed by methods well known in the art.

Stability determination

All stability trials are made using the same set up. The method are:

The enzyme is incubated under the relevant conditions (1–4). Samples are taken at various time points, e.g., after 0, 5, 10, 15 and 30 minutes and diluted 25 times (same dilution for all taken samples) in assay buffer (0.1 M 50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

Specific activity determination

The specific activity is determined using the Phadebas assay (Pharmacia) as activity/mg enzyme. The manufactures instructions are followed (see also below under "Assay for α-amylase activity).

Assays for α-Amylase Activity

1. Phadebas assay

α-amylase activity is determined by a method employing Phadebas® tablets as substrate. Phadebas tablets (Phadebas® Amylase Test, supplied by Pharmacia Diagnostic) contain a cross-linked insoluble blue-colored starch polymer which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 nM boric acid, 0.1 mM $CaCl_2$, pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolyzed by the α-amylase giving soluble blue fragments. The absorbance of the resulting blue solution, measured spectrophotometrically at 620 nm, is a function of the amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given α-amylase will hydrolyze a certain amount of substrate and a blue colour will be produced. The colour intensity is measured at 620 nm. The measured absorbance is directly proportional to the specific activity (activity/mg of pure α-amylase protein) of the α-amylase in question under the given set of conditions.

2. Alternative method

α-amylase activity is determined by a method employing the PNP-G7 substrate. PNP-G7 which is a abbreviation for p-nitrophenyl-α,D-maltoheptaoside is a blocked oligosaccharide which can be cleaved by an endo-amylase. Following the cleavage, the α-Glucosidase included in the kit digest the substrate to liberate a free PNP molecule which has a yellow colour and thus can be measured by visible spectophometry at λ=405 nm. (400–420 nm.). Kits containing PNP-G7 substrate and α-Glucosidase is manufactured by Boehringer-Mannheim (cat.No. 1054635).

To prepare the substrate one bottle of substrate (BM 1442309) is added to 5 ml buffer (BM1442309). To prepare the α-Glucosidase one bottle of α-Glucosidase (BM 1462309) is added to 45 ml buffer (BM1442309). The working solution is made by mixing 5 ml α-Glucosidase solution with 0.5 ml substrate.

The assay is performed by transforming 20 µl enzyme solution to a 96 well microtitre plate and incubating at 25° C. 200 µl working solution, 25° C. is added. The solution is mixed and pre-incubated 1 minute and absorption is measured every 15 sec. over 3 minutes at OD 405 nm.

The slope of the time dependent absorption-curve is directly proportional to the specific activity (activity per mg enzyme) of the α-amylase in question under the given set of conditions.

General method for random mutagenesis by use of the DOPE program

The random mutagenesis may be carried out by the following steps:

1. Select regions of interest for modification in the parent enzyme
2. Decide on mutation sites and non-mutated sites in the selected region
3. Decide on which kind of mutations should be carried out, e.g. with respect to the desired stability and/or performance of the variant to be constructed
4. Select structurally reasonable mutations.
5. Adjust the residues selected by step 3 with regard to step 4.
6. Analyze by use of a suitable dope algorithm the nucleotide distribution.
7. If necessary, adjust the wanted residues to genetic code realism (e.g., taking into account constraints resulting from the genetic code (e.g. in order to avoid introduction of stop codons)) (the skilled person will be aware that some codon combinations cannot be used in practice and will need to be adapted)
8. Make primers
9. Perform random mutagenesis by use of the primers
10. Select resulting α-amylase variants by screening for the desired improved properties.

Suitable dope algorithms for use in step 6 are well known in the art. One algorithm is described by Tomandl, D. et al., Journal of Computer-Aided Molecular Design, 11 (1997), pp. 29–38). Another algorithm, DOPE, is described in the following:

The dope program

The "DOPE" program is a computer algorithm useful to optimize the nucleotide composition of a codon triplet in such a way that it encodes an amino acid distribution which resembles most the wanted amino acid distribution. In order to assess which of the possible distributions is the most similar to the wanted amino acid distribution, a scoring function is needed. In the "Dope" program the following function was found to be suited:

$$s \equiv \prod_{i=1}^{N}\left(\frac{x_i^{y_i}(1-x_i)^{1-y_i}}{y_i^{y_i}(1-y_i)^{1-y_i}}\right)^{w_i},$$

where the $x_1$'s are the obtained amounts of amino acids and groups of amino acids as calculated by the program, $y_1$'s are the wanted amounts of amino acids and groups of amino acids as defined by the user of the program (e.g. specify which of the 20 amino acids or stop codons are wanted to be introduced, e.g. with a certain percentage (e.g. 90% Ala, 3% Ile, 7% Val), and $w_1$'s are assigned weight factors as defined by the user of the program (e.g., depending on the importance of having a specific amino acid residue inserted into the position in question). N is 21 plus the number of amino acid groups as defined by the user of the program. For purposes of this function 0° is defined as being 1.

A Monte-Carlo algorithm (one example being the one described by Valleau, J. P. & Whittington, S. G. (1977) A guide to Mont Carlo for statistical mechanics: 1 Highways. In "Stastistical Mechanics, Part A" Equlibrium Techniqeues ed. B. J. Berne, New York: Plenum) is used for finding the maximum value of this function. In each iteration the following steps are performed:

1. A new random nucleotide composition is chosen for each base, where the absolute difference between the current and the new composition is smaller than or equal to d for each of the four nucleotides G,A,T,C in all three positions of the codon (see below for definition of d).

2. The scores of the new composition and the current composition are compared by the use of the function s as described above. If the new score is higher or equal to the score of the current composition, the new composition is kept and the current composition is changed to the new one. If the new score is smaller, the probability of keeping the new composition is $\exp(1000(new\_score\_current\_score))$.

A cycle normally consists of 1000 iterations as described above in which d is decreasing linearly from 1 to 0. One hundred or more cycles are performed in an optimization process. The nucleotide composition resulting in the highest score is finally presented.

EXAMPLES

Example 1
Example on Homology building of Termamyl™

The overall homology of the *B. licheniformis* $_\alpha$-amylase (in the following referred to as Termamyl™) to other Termamyl-like $_\alpha$-amylases is high and the percent similarity is extremely high. The similarity calculated for Termamyl™ to BSG (the *B. stearothermophilus* $_\alpha$-amylase having SEQ ID NO: 3), and BAN (the *B. amyloliquefaciens* $_\alpha$-amylase having SEQ ID NO: 5) using the University of Wisconsin Genetics Computer Group's program GCG gave 89% and 78%, respectively. TERM has a deletion of 2 residues between residue G180 and K181 compared to BAN™ and BSG. BSG has a deletion of 3 residues between G371 and I372 in comparison with BAN™ and Termamyl™. Further BSG has a C-terminal extension of more than 20 residues compared to BAN™ and Termamyl™. BANT™ has 2 residues less and Termamyl has one residue less in the N-terminal compared to BSG.

The structure of the *B. licheniformis* (Termamyl™) and of the *B. amyloliquefaciens* $_\alpha$-amylase (BAN™), respectively, was model built on the structure disclosed in Appendix 1 of WO 96/23974. The structure of other Termamyl-like $_\alpha$-amylases (e.g. those disclosed herein) may be built analogously.

In comparison with the $_\alpha$-amylase used for elucidating the present structure, Termamyl™ differs in that it lacks two residues around 178–182. In order to compensate for this in the model structure, the HOMOLOGY program from BIO-SYM was used to substitute the residues in equivalent positions in the structure (not only structurally conserved regions) except for the deletion point. A peptide bond was established between G179(G177) and K180(K180) in Termamyl™ (BAN™). The close structural relationship between the solved structure and the model structure (and thus the validity of the latter) is indicated by the presence of only very few atoms found to be too close together in the model.

To this very rough structure of Termamyl™ was then added all waters (605) and ions (4 Calcium and 1 Sodium) from the solved structure (See Appendix 1 of WO 96/23874) at the same coordinates as for said solved structure using the INSIGHT program. This could be done with only few overlaps—in other words with a very nice fit. This model structure were then minimized using 200 steps of Steepest descent and 600 steps of Conjugated gradient (see Brooks et al 1983, J. Computational Chemistry 4, p.187–217). The minimized structure was then subjected to molecular dynamics, 5 ps heating followed by up to 200 ps equilibration but more than 35 ps. The dynamics as run with the Verlet algorithm and the equilibration temperature 300K were kept using the Behrendsen coupling to a water bath (Berendsen et. al., 1984, J. Chemical Physics 81, p. 3684–3690). Rotations and translations were removed every pico second.

Example 2
Method of extracting important regions for identifying $_\alpha$-amylase variants with improved pH stability and altered temperature activity The X-ray structure and/or the model build structure of the enzyme of interest, here SP722 and Termamyl™, are subjected to molecular dynamics simulations. The molecular dynamics simulation are made using the CHARMM (from Molecular simulations (MSI)) program or other suited program like, e.g., DISCOVER (from MSI). The molecular dynamic analysis is made in vacuum, or more preferred including crystal waters, or with the enzyme embedded in water, e.g., a water sphere or a water box. The simulation are run for 300 pico seconds (ps) or more, e.g., 300–1200 ps. The isotropic fluctuations are extracted for the CA carbons of the structures and compared between the structures. Where the sequence has deletions and/or insertions the isotropic fluctuations from the other structure are inserted thus giving 0 as difference in isotropic fluctuation. For explanation of isotropic fluctuations see the CHARMM manual (obtainable from MSI).

The molecular dynamics simulation can be done using standard charges on the chargeable amino acids. This is Asp and Glu are negatively charged and Lys and Arg are positively charged. This condition resembles the medium pH of approximately 7. To analyze a higher or lower pH, titration of the molecule can be done to obtain the altered pKa's of the standard titrateable residues normally within pH 2–10; Lys, Arg, Asp, Glu, Tyr and His. Also Ser, Thr and Cys are titrateable but are not taking into account here. Here the altered charges due to the pH has been described as both Asp and Glu are negative at high pH, and both Arg and Lys are uncharged. This imitates a pH around 10 to 11 where the titration of Lys and Arg starts, as the normal pKa of these residues are around 9–11.

1. The approach used for extracting important regions for identifying $_\alpha$-amylase variants with high pH stability:

The important regions for constructing variants with improved pH stability are the regions which at the extreme pH display the highest mobility, i.e., regions having the highest isotropic fluctuations.

Such regions are identified by carrying out two molecular dynamics simulations: i) a high pH run at which the basic amino acids, Lys and Arg, are seen as neutral (i.e. not protonated) and the acidic amino acids, Asp and Glu, have the charge (−1) and ii) a neutral pH run with the basic amino acids, Lys and Arg, having the net charge of (+1) and the acidic amino acids having a charge of (−1).

The two run are compared and regions displaying the relatively higher mobility at high pH compared to neutral pH analysis were identified.

Introduction of residues improving general stability, e.g., hydrogen bonding, making the region more rigid (by mutations such as Proline substitutions or replacement of Glycine residues), or improving the charges or their interaction, improves the high pH stability of the enzyme.

2. The approach used for extracting regions for identifying $\alpha$-amylase variants with increased activity at medium temperatures:

The important regions for constructing variants with increased activity at medium temperature was found as the difference between the isotropic fluctuations in SP722 and Termamyl, i.e., SP722 minus Termamyl CA isotrophic fluctuations, The regions with the highest mobility in the isotrophic fluctuations were selected. These regions and there residues were expected to increase the activity at medium temperatures. The activity of an alpha-amylase is only expressed if the correct mobility of certain residues are present. If the mobility of the residues is too low the activity is decreased or abandoned.

Example 3

Construction, by localized random, doped mutagenesis, of Termamyl-like $\alpha$-amylase variants having an improved Ca2+ stability at medium temperatures compared to the parent enzyme To improve the stability at low calcium concentration of $\alpha$-amylases random mutagenesis in pre-selected region was performed.

Region: Residue:
SAI: R181-W189

The DOPE software (see Materials and Methods) was used to determine spiked codons for each suggested change in the SA1 region minimizing the amount of stop codons (see table 1). The exact distribution of nucleotides was calculated in the three positions of the codon to give the suggested population of amino acid changes. The doped regions were doped specifically in the indicated positions to have a high chance of getting the desired residues, but still allow other possibilities.

TABLE 1

| Distribution of amino acid residues for each position | |
| --- | --- |
| R181 | 72% R, 2% N, 7% Q, 4% H, 4% K, 11% S |
| G182 | 73% G, 13% A, 12% S, 2% T |
| K185 | 95% K, 5% R |
| A186 | 50% A, 4% N, 6% D, 1% E, 1% G, 1% K, 5% S, 31% T |
| W187 | 100% W |
| D188 | 100% D |
| W189 | 92% W, 8% S |

The resulting doped oligonucleotide strand is shown in table 2 as sense strand: with the wild type nucleotide and amino acid sequences and the distribution of nucleotides for each doped position.

TABLE 2

| Position | 181 | 182 | 185 | 186 | 187 | 188 | 189 |
| --- | --- | --- | --- | --- | --- | --- | --- |
| Amino acid seq. | Arg | Gly | Lys | Ala | Thr | Asp | Thr |
| Wt nuc. seq. | cga | ggt | aaa | gct | tgg | gat | tgg |

Forward primer (SEQ ID NO: 15):
FSA: 5'-caa aat cgt atc tac aaa ttc 123 456 a7g 8910 tgg gat t11g gaa gta gat tcg gaa aat-3'
Distribution of nucleotides for each doped Position
1: 35% A, 65% C
2: 83% G, 17% A
3: 63% G, 37% T
4: 86% G. 14% A
5: 85% G, 15% C
6: 50% T. 50% C
7: 95% A, 5%G
8: 58% G, 37% A, 5% T
9: 86% C, 13% A, 1% G
10: 83% T, 17% G
11: 92% G, 8% C
Reverse primer (SEQ ID NO: 16):
RSA: 5'-gaa ttt gta gat acg att ttg-3'
Random mutagenesis The spiked oligonucleotides apparent from Table 2 (which by a common term is designated FSA) and reverse primers RSA for the SA1 region and specific SEQ ID NO: 2: SP722 primers covering the SacII and the DraIII sites are used to generate PCR-library-fragments by the overlap extension method (Horton et al., Gene, 77 (1989), pp. 61–68) with an overlap of 21 base pairs. Plasmid pJE1 is template for the Polymerase Chain Reaction. The PCR fragments are cloned in the E. coli/Bacillus shuttle vector pDork101 (see Materials and Methods) enabling mutagenesis in E. coli and immediate expression in Bacillus subtilis preventing lethal accumulation of amylases in E. coli. After establishing the cloned PCR fragments in E. coli, a modified pUC19 fragment is digested out of the plasmid and the promoter and the mutated Termamyl gene is physically connected and expression can take place in Bacillus.

Screening

The library may be screened in the low calcium filter assays described in the "Material and Methods" section above.

Example 4

Construction of variants of amylase SEQ ID NO: 1 (SP690)

The gene encoding the amylase from SEQ ID NO: 1 is located in a plasmid pTVB106 described in WO96/23873. The amylase is expressed from the amyL promoter in this construct in Bacillus subtilis.

A variant of the protein is delta(T183-G184) +Y243F+ Q391E+K444Q. Construction of this variant is described in WO96/23873.

Construction of delta(T183-G184)+N195F by the mega-primer method as described by Sarkar and Sommer, (1990), BioTechniques 8: 404–407.

Gene specific primer B1 (SEQ ID NO: 17) and mutagenic primer 101458 (SEQ ID NO: 19) were used to amplify by PCR an approximately 645 bp DNA fragment from a pTVB106-like plasmid (with the delta(T183-G184) mutations in the gene encoding the amylase from SEQ ID NO: 1).

The 645 bp fragment was purified from an agarose gel and used as a mega-primer together with primer Y2 (SEQ ID NO: 18) in a second PCR carried out on the same template.

The resulting approximately 1080 bp fragment was digested with restriction enzymes BstEII and AflIII and the resulting approximately 510 bp DNA fragment was purified and ligated with the pTVB106-like plasmid (with the delta (T183-G184) mutations in the gene encoding the amylase from SEQ ID NO: 1) digested with the same enzymes. Competent Bacillus subtilis SHA273 (amylase and protease low) cells were transformed with the ligation and Chlorampenicol resistant transformants and was checked by DNA sequencing to verify the presence of the correct mutations on the plasmid.
primer B1: (SEQ ID NO: 17)
5' CGA TTG CTG ACG CTG TTA TTT GCG 3'
primer Y2: (SEQ ID NO: 18)
5' CTT GTT CCC TTG TCA GAA CCA ATG 3'
primer 101458 (SEQ ID NO: 19):
5'GT CAT AGT TGC CGA AAT CTG TAT CGA CTT C 3'

The construction of variant: delta(T183-G184)+K185R+ A186T was carried out in a similar way except that mutagenic primer 101638 was used. primer 101638: (SEQ ID NO: 20)

5' CC CAG TCC CAC GTA CGT CCC CTG AAT TTA TAT ATT TTG 3'

Variants: delta(T183-G184)+A186T, delta(T183-G184)+A186I, delta(T183-G184)+A186S, delta(T183-G184)+A186N are constructed by a similar method except that pTVB106-like plasmid (carrying variant delta(T183-G184)+K185R+A186T) is used as template and as the vector for the cloning purpose. The mutagenic oligonucleotide (Oligo 1) is:

5' CC CAG TCC CAG NTCTTT CCC CTG AAT TTA TAT ATT TTG 3'(SEQ ID NO: 21)

N represents a mixture of the four bases: A, C, G, and T used in the synthesis of the mutagenicoli-gonucleotide. Sequencing of transformants identifies the correct codon for amino acid position 186 in the mature amylase.

Variant: delta(T183-G184)+K185R+A186T+N195F is constructed as follows:

PCR is carried out with primer x2 (SEQ ID NO: 22) and primer 101458 (SEQ ID NO: 19) on pTVB106-like plasmid (with mutations delta(T183-G184)+K185R+A186T). The resulting DNA fragment is used as a mega-primer together with primer Y2 (SEQ ID NO: 18) in a PCR on pTVB106-like plasmid (with mutations delta(T183-G184) +N195). The product of the second PCR is digested with restriction endonucleases Acc65I and AflIII and cloned into pTVB106 like plasmid (delta(T183-G184)+N195F) digested with the same enzymes.

primer x2: (SEQ ID NO: 22)
5' GCG TGG ACA AAG TTT GAT TTT CCT G 3'

Variant: delta(T183-G184)+K185R+Al86T+N195F+Y243F+Q391E+K444Q is constructed as follows:

PCR is carried out with primer x2 and primer 101458 on pTVB106-like plasmid (with mutations delta(T183-G184)+K185R+A186T). The resulting DNA fragment is used as a mega-primer together with primer Y2 in a PCR on pTVB106 like plasmid (with mutations delta(T183-G184)+Y243F+Q391E+K444Q). The product of the second PCR is digested with restriction endonucleases Acc65I and AflIII and cloned into pTVB106 like plasmid (delta(T183-G184)+Y243F+Q391E+K444Q) digested with the same enzymes.

Example 5

Construction of site-directed α-amylase variants in the parent SP722 α-amylase (SEQ ID NO: 2)

Construction of variants of amylase SEQ ID NO: 2 (SP722) is carried out as described below.

The gene encoding the amylase from SEQ ID NO: 2 is located in a plasmid pTVB112 described in WO 96/23873. The amylase is expressed from the amyL promoter in this construct in *Bacillus subtilis*.

Construction of delta(D183-G184)+V56I by the mega-primer method as described by Sarkar and Sommer, 1990 (BioTechniques 8: 404–407).

Gene specific primer DA03 and mutagenic primer DA07 are used to amplify by PCR an approximately 820 bp DNA fragment from a pTVB112-like plasmid (with the delta (D183-G184) mutations in the gene encoding the α-amylase shown in SEQ ID NO: 2.

The 820 bp fragment is purified from an agarose gel and used as a mega-primer together with primer DA01 in a second PCR carried out on the same template.

The resulting approximately 920 bp fragment is digested with restriction enzymes NgoM I and Aat II and the resulting approximately 170 bp DNA fragment is purified and ligated with the pTVB112-like plasmid (with the delta(D183-G184) mutations in the gene encoding the amylase shown in SEQ ID NO: 2) digested with the same enzymes. Competent *Bacillus subtilis* SHA273 (amylase and protease low) cells are transformed with the ligation and Chlorampenicol resistant transformants are checked by DNA sequencing to verify the presence of the correct mutations on the plasmid.

primer DA01: (SEQ ID NO: 23)
5' CCTAATGATGGGAATCACTGG 3'
primer DA03: (SEQ ID NO:24)
5'GCATTGGATGCTTTTGAACAACCG 3'
primer DA07 (SEQ ID NO:25):
5' CGCAAAATGATATCGGGTATGGAGCC 3'

Variants: delta(D183-G184)+K108L, delta(D183-G184)+K108Q, delta(D183-G184)+K108E, delta(D183-G184)+K108V, were constructed by the mega-primer method as described by Sarkar and Sommer ,1990 (BioTechniques 8: 404–407):

PCR is carried out with primer DA03 and mutagenesis primer DA20 on pTVB112-like plasmid (with mutations delta(D183-G184)). The resulting DNA fragment is used as a mega-primer together with primer DA01 in a PCR on pTVB112-like plasmid (with mutations delta(D183-G184)). The approximately 920 bp product of the second PCR is digested with restriction endonucleases Aat II and Mlu I and cloned into pTVB112-like plasmid (delta(D183-G184)) digested with the same enzymes. primer DA20 (SQ ID NO:26):

5'GTGATGAACCACSWAGGTGGAGCTGATGC 3'

S represents a mixture of the two bases: C and G used in the synthesis of the mutagenic oligonucleotide and W represents a mixture of the two bases: A and T used in the synthesis of the mutagenic oligonucleotide.

Sequencing of transformants identifies the correct codon for amino acid position 108 in the mature amylase.

Construction of the variants: delta(D183-G184)+D168A, delta(D183-G184)+D168I, delta(D183-G184)+D168V, delta(D183-G184)+D168T is carried out in a similar way except that mutagenic primer DA14 is used. primer DA14 (SEQ ID NO:27):

5'GATGGTGTATGGRYCAATCACGACAATTCC 3'

R represents a mixture of the two bases: A and G used in the synthesis of the mutagenic oligonucleotide and Y represents a mixture of the two bases: C and T used in the synthesis of the mutagenic oligonucleotide.

Sequencing of transformants identifies the correct codon for amino acid position 168 in the mature amylase.

Construction of the variant: delta(D183-G184)+Q169N is carried out in a similar way except that mutagenic primer DA15 is used.

primer DA15 (SEQ ID NO:28):
5'GGTGTATGGGATAACTCACGACAATTCC 3'

Construction of the variant: delta(D183-G184)+Q169L is carried out in a similar way except that mutagenic primer DA16 is used.

primer DA16 (SEQ ID NO:29)
5'GGTGTATGGGATCTCTCACGACAATTCC 3'

Construction of the variant: delta(D183-G184)+Q172N is carried out in a similar way except that mutagenic primer DA17 is used.

primer DA17 (SEQ ID NO:30):
5'GGGATCAATCACGAAATTTCCAAAATCGTATC 3'

Construction of the variant: delta(D183-G184)+Q172L is carried out in a similar way except that mutagenic primer DA18 is used.

primer DA18 (SEQ ID NO:31):
5'GGGATCAATCACGACTCTTCCAAAATCGTATC 3'

Construction of the variant: delta(D183-G184)+L201I is carried out in a similar way except that mutagenic primer DA06 is used.

primer DA06 (SEQ ID NO:32):
    5'GGAAATTATGATTATATCATGTATGCAGATGTAG 3'

Construction of the variant: delta(D183-G184)+K269S is carried out in a similar way except that mutagenic primer DA09 is used.

primer DA09 (SEQ ID NO:33):
    5'GCTGAATTTTGGTCGAATGATTTAGGTGCC 3'

Construction of the variant: delta(D183-G184)+K269Q is carried out in a similar way except that mutagenic primer DAli is used.

primer DA11 (SEQ ID NO:34):
    5'GCTGAATTTTGGTCGAATGATTTAGGTGCC 3'

Construction of the variant: delta(D183-G184)+N270Y is carried out in a similar way except that mutagenic primer DA21 is used.

primer DA21 (SEQ ID NO:35):
    5'GAATTTTGGAAGTACGATTTAGGTCGG 3'

Construction of the variants: delta(D183-G184)+L272A, delta(D183-G184)+L272I, delta(D183-G184)+L272V, delta(D183-G184)+L272T is carried out in a similar way except that mutagenic primer DA12 is used.

primer DA12 (SEQ ID NO:36):
    5'GGAAAAACGATRYCGGTGCCTTGGAGAAC 3'

R represents a mixture of the two bases: A and G used in the synthesis of the mutagenic oligonucleotide and Y represents a mixture of the two bases: C and T used in the synthesis of the mutagenic oligonucleotide. Sequencing of transformants identifies the correct codon for amino acid position 272 in the mature amylase.

Construction of the variants: delta(D183-G184)+L275A, delta(D183-G184)+L275I, delta(D183-G184)+L275V, delta(D183-G184)+L275T is carried out in a similar way except that mutagenic primer DA13 is used.

primer DA13 (SEQ ID NO:37):
    5'GATTTAGGTGCCTRYCAGAACTATTTA 3'

R represents a mixture of the two bases: A and G used in the synthesis of the mutagenic oligonucleotide and Y represents a mixture of the two bases: C and T used in the synthesis of the mutagenic oligonucleotide. Sequencing of transformants identifies the correct codon for amino acid position 275 in the mature amylase.

Construction of the variant: delta(D183-G184)+Y295E is carried out in a similar way except that mutagenic primer DA08 is used.

primer DA08 (SEQ ID NO:38):
    5' CCCCCTTCATGAGAATCTTTATAACG 3'

Construction of delta(D183-G184)+K446Q by the megaprimer method as described by Sarkar and Sommer,1990 (BioTechniques 8: 404–407):

Gene specific primer DA04, annealing 214–231 bp downstream relative to the STOP-codon and mutagenic primer DA10 were used to amplify by PCR an approximately 350 bp DNA fragment from a pTVB112-like plasmid (with the delta(D183-G184) mutations in the gene encoding the amylase depicted in SEQ ID NO: 2).

The resulting DNA fragment is used as a mega-primer together with primer DA05 in a PCR on pTVB112 like plasmid (with mutations delta(D183-G184)). The app. 460 bp product of the second PCR is digested with restriction endonucleases SnaB I and Not I and cloned into pTVB112 like plasmid (delta(D183-G184)) digested with the same enzymes.

primer DA04 (SEQ ID NO:39):
    5'GAATCCGAACCTCATTACACATTCG 3'
    primer DA05 (SEQ ID NO:40):
    5' CGGATGGACTCGAGAAGGAAATACCACG 3'
    primer DA10 (SEQ ID NO:41):
    5' CGTAGGGCAAAATCAGGCCGGTCAAGTTTGG 3'

Construction of the variants: delta(D183-G184)+K458R is carried out in a similar way except that mutagenic primer DA22 is used.

primer DA22 (SEQ ID NO:42):
    5' CATAACTGGAAATCGCCCGGGAACAGTTACG 3'

Construction of the variants: delta(D183-G184)+P459S and delta(D183-G184)+P459T is carried out in a similar way except that mutagenic primer DA19 is used.

primer DA19 (SEQ ID NO:43):
    5' CTGGAAATAAAWCCGGAACAGTTACG 3'

W represents a mixture of the two bases: A and T used in the synthesis of the mutagenic oligonucleotide. Sequencing of transformants identifies the correct codon for amino acid position 459 in the mature amylase.

Construction of the variants: delta(D183-G184)+T461P is carried out in a similar way except that mutagenic primer DA23 is used.

primer DA23 (SEQ ID NO:44):
    5'GGAAATAAACCAGGACCCGTTACGATCAATGC 3'

Construction of the variant: delta(D183-G184)+K142R is carried out in a similar way except that mutagenic primer DA32 is used.

Primer DA32 (SEQ ID NO: 45):
    5'GAGGCTTGGACTAGGTTTGATTTTCCAG 3'

Construction of the variant: delta(D183-G184)+K269R is carried out in a similar way except that mutagenic primer DA31 is used.

Primer DA31 (SEQ ID NO: 46):
    5'GCTGAATTTTGGCGCAATGATTTAGGTGCC 3'

Example 6

Construction of site-directed $\alpha$-amylase variants in the parent Termamyl $\alpha$-amylase (SEQ ID NO: 4)

The amyL gene, encoding the Termamyl $\alpha$-amylase is located in plasmid pDN1528 described in WO 95/10603 (Novo Nordisk). Variants with substitutions N265R and N265D, respectively, of said parent $\alpha$-amylase are constructed by methods described in WO 97/41213 or by the "megaprimer" approach described above.

Mutagenic oligonucleotides are:
    Primer bl1 for the N265R substitution:
    5'PCC AGC GCG CCT AGG TCA CGC TGC CAA TAT TCA G (SEQ ID NO: 56)
    Primer bl2 for the N265D substitution:
    5'PCC AGC GCG CCT AGG TCA TCC TGC CAA TAT TCA G (SEQ ID NO: 57)

P represents a phosphate group.

Example 7

Determination of pH stability at alkaline pH of variants of the parent $\alpha$-Amylase having the amino acid sequence shown in SEQ ID NO:2.

In this serie of analysis purified enzyme samples were used. The measurements were made using solutions of the respective variants in 100 mM CAPS buffer adjusted to pH 10.5. The solutions were incubated at 75° C.

After incubation for 20 and 30 min the residual activity was measured using the PNP-G7 assay (described in the "Materials and Methods" section above). The residual activity in the samples was measured using Britton Robinson buffer pH 7.3. The decline in residual activity was measured relative to a corresponding reference solution of the same enzyme at 0 minutes, which has not been incubated at high pH and 75° C.

The percentage of the initial activity as a function is shown in the table below for the parent enzyme (SEQ ID NO: 2) and for the variants in question.

| Variant | Residual activity after 20 min | Residual activity after 30 min |
|---|---|---|
| $\Delta^{(D183-G184)+M323L}$ | 56% | 44% |
| $\Delta^{(D183-G184)+M323L+R181S}$ | 67% | 55% |
| $\Delta^{(D183-G184)+M323L+A186T}$ | 62% | 50% |

In an other series of analysis culture supernatants were used. The measurements were made using solutions of the respective variants in 100 mM CAPS buffer adjusted to pH 10.5. The solutions were incubated at 80° C.

After incubation for 30 minutes the residual activity was measured using the Phadebas assay (described in the "Materials and Method" secion above. The residual activity in the samples was measured using Britton Robinson buffer pH 7.3. The decline in residual activity was measured relative to a corresponding reference solution of the same enzyme at 0 minutes, which has not been incubated at high pH and 80° C.

The percentage of the initial activity as a function is shown in the table below for the parent enzyme (SEQ ID NO: 2) and for the variants in question.

| Variant | Residual activity after 30 min |
|---|---|
| $\Delta^{(D183-G184)}$ | 4% |
| $\Delta^{(D183-G184)+P459T}$ | 25% |
| $\Delta^{(D183-G184)+K458R}$ | 31% |
| $\Delta^{(D183-G184)+K311R}$ | 10% |

Example 8

Determination of calcium stability at alkaline pH of variants of the parent $\alpha$-Amylase having the amino acid sequence shown in SEQ ID NO: 1, SEQ ID NO: 2 and SEQ ID NO: 4.

A: Calcium stability of variants of the sequence in SEQ ID NO: 1

The measurement were made using solutions of the respective variants in 100 mM CAPS buffer adjusted to pH 10.5 to which polyphosphate was added (at time t=0) to give a final concentration of 2400 ppm. The solutions were incubated at 50° C.

After incubation for 20 and 30 minutes the residual activity was measured using the PNP-G7 assay (described above). The residual activity in the samples was measured using Britton Robinson buffer pH 7.3. The decline in residual activity was measured relative to a corresponding reference solution of the same enzyme at 0 minutes, which has not been incubated at high pH and 50° C.

The percentage of the initial activity as a function is shown in the table below for the parent enzyme (SEQ ID NO: 1) and for the variants in question.

| Variant | Residual activity after 20 min | Residual activity after 30 min |
|---|---|---|
| $\Delta^{(T183-G184)}$ | 32% | 19% |
| $\Delta^{(T183-G184)+A186T}$ | 36% | 23% |

-continued

| Variant | Residual activity after 20 min | Residual activity after 30 min |
|---|---|---|
| $\Delta^{(T183-G184)+K185R+A186T}$ | 45% | 29% |
| $\Delta^{(T183-G184)+A186I}$ | 35% | 20% |
| $\Delta^{(T183-G184)+N195F}$ | 44% | n.d. | n.d. = Not determinated

B: Calcium stability of variants of the sequence in SEQ ID NO: 2

In this serie of analysis purified samples of enzymes were used. The measurement were made using solutions of the respective variants in 100 mM CAPS buffer adjusted to pH 10.5 to which polyphosphate was added (at time t=0) to give a final concentration of 2400 ppm. The solutions were incubated at 50° C.

After incubation for 20 and 30 minutes the residual activity was measured using the PNP-G7 assay (described above). The residual activity in the samples was measured using Britton Robinson buffer pH 7.3. The decline in residual activity was measured relative to a corresponding reference solution of the same enzyme at 0 minutes, which has not been incubated at high pH and 50° C.

The percentage of the initial activity as a function is shown in the table below for the parent enzyme (SEQ ID NO: 2) and for the variants in question.

| Variant | Residual activity after 20 min | Residual activity after 30 min |
|---|---|---|
| $\Delta^{(D183-G184)+M323L}$ | 21% | 13% |
| $\Delta^{(D183-G184)+M323L+R181S}$ | 32% | 19% |
| $\Delta^{(D183-G184)+M323L+A186T}$ | 28% | 17% |
| $\Delta^{(D183-G184)+M323L+A186R}$ | 30% | 18% |

| Variant | Residual activity after 20 min | Residual activity after 30 min |
|---|---|---|
| $\Delta^{(D183-G184)}$ | 30% | 20% |
| $\Delta^{(D183-G184)+N195F}$ | 55% | 44% |

In this serie of analysis culture supernatants were used. The measurement were made using solutions of the respective variants in 100 mM CAPS buffer adjusted to pH 10.5 to which polyphosphate was added (at time t=0) to give a final concentration of 2400 ppm. The solutions were incubated at 50° C.

After incubation for 30 minutes the residual activity was measured using the Phadebas assay as described above. The residual activity in the samples was measured using Britton Robinson buffer pH 7.3. The decline in residual activity was measured relative to a corresponding reference solution of the same enzyme at 0 minutes, which has not been incubated at high pH and 50° C.

The percentage of the initial activity as a function is shown in the table below for the parent enzyme (SEQ ID NO: 2) and for the variants in question.

| Variant | Residual activity after 30 min |
|---|---|
| A$^{(D183-G184)}$ | 0% |
| A$^{(D183-G184)+P459T}$ | 19% |
| A$^{(D183-G184)+K458R}$ | 18% |
| A$^{(D193-G184)+T461P}$ | 13% |
| A$^{(D183-G184)+E346Q+K385R}$ | 4% |

C: Calcium stability of variants of the sequence in SEQ ID NO: 4

The measurement were made using solutions of the respective variants in 100 mM CAPS buffer adjusted to pH 10.5 to which polyphosphate was added (at time t=0) to give a final concentration of 2400 ppm. The solutions were incubated at 60° C. for 20 minutes.

After incubation for 20 minutes the residual activity was measured using the PNP-G7 assay (described above). The residual activity in the samples was measured using Britton Robinson buffer pH 7.3. The decline in residual activity was measured relative to a corresponding reference solution of the same enzyme at 0 minutes, which has not been incubated at high pH and 60° C.

The percentage of the initial activity as a function is shown in the table below for the parent enzyme (SEQ ID NO: 4) and for the variants in question.

| Variant | Residual activity after 20 min |
|---|---|
| Termamyl (SEQ ID NO: 4) | 17% |
| N265R | 28% |
| N265D | 25% |

Example 9

Activity measurement at medium temperature of -Amylases having the amino acid sequence shown in SEQ ID NO: 1.

A:$_{60}$ -Amylase activity of variants of the sequence in SEQ ID NO:1

The measurement were made using solutions of the respective variants in 50 mM Britton Robinson buffer adjusted to pH 7.3 and using the Phadebas assay described above. The activity in buffer pH 7.3 and at 25° C. using 50 mM CAPS buffer pH 10.5.

The temperature dependent activity and the percentage of the activity at 25° C. relative to the activity at 37° C. is shown in the table below for the parent enzyme (SEQ ID NO: 1) and for the variants in question.

| Variant | NU/mg 25° C. | NU/mg 37° C. | NU (25° C.)/ NU (37° C.) |
|---|---|---|---|
| SP690 | 1440 | 35000 | 4.1% |
| A$^{(T183-G184)}$ | 2900 | 40000 | 7.3% |
| A$^{(T183-G184)+K269S}$ | 1860 | 12000 | 15.5% |
| A$^{(Q174)}$ | 3830 | 38000 | 7.9% |

Another measurement was made using solutions of the respective variants in 50 mM Britton Robinson buffer adjusted to pH 7.3 and using the Phadebas assay described above. The activity in the samples was measured at 37° C. and 50° C. using 50 mM Britton Robinson buffer pH 7.3.

The temperature dependent activity and the percentage of the activity at 37° C. relative to the activity at 50° C. is shown in the table below for the parent enzyme (SEQ ID NO: 1) and for the variants in question.

| Variant | NU/mg 37° C. | NU/mg 50° C. | NU(37° C.) / NU(50° C.) |
|---|---|---|---|
| SP690 (seq ID NO: 1) | 13090 | 21669 | 60% |
| K269Q | 7804 | 10063 | 78% |

B: $_\alpha$-Amylase activity of variants of the sequence in SEQ ID NO:2

The measurement were made using solutions of the respective variants in 50 mM Britton Robinson buffer adjusted to pH 7.3 and using the Phadebas assay described above. The activity in the samples was measured at both 25° C. and 37° C. using 50 mM Britton Robinson buffer pH 7.3.

The temperature dependent activity and the percentage of the activity at 25° C. relative to the activity at 37° C. is shown in the table below for the parent enzyme (SEQ ID NO: 2) and for the variants in question.

| Variant | NU/mg 25° C. | NU/mg 37° C. | NU(25° C.) / NU(37° C.) |
|---|---|---|---|
| A$^{(D183-G184)}$ + M323L | 3049 | 10202 | 30% |
| A$^{(D183-G184)}$ + M323L + R181S | 18695 | 36436 | 51% |

C: $_\alpha$-Amylase activity of variants of the sequence in SEQ ID NO:4

The measurement were made using solutions of the respective variants in 50 mM Britton Robinson buffer adjusted to pH 7.3 and using the Phadebas assay described above. The activity in the samples was measured at both 37° C. using 50 mM Britton Robinson buffer pH 7.3 and at 60° C. using 50 mM CAPS buffer pH 10.5.

The temperature dependent activity and the percentage of the activity at 37° C. relative to the activity at 60° C. is shown in the table below for the parent enzyme (SEQ ID NO: 4) and for the variants in question.

| Variant | NU/mg 37° C. | NU/mg 60° C. | NU(37° C.) / NU(60° C.) |
|---|---|---|---|
| Termamyl | 7400 | 4350 | 170% |
| Q264S | 10000 | 4650 | 215% |

Example 10

Construction of variants of parent hybrid BAN:1–300/Termamyl:301–483 $_\alpha$-amylase Plasmid pTVB191 contains the gene encoding hybrid $_\alpha$-amylase BAN:1–300/Termamyl:301–483 as well as an origin of replication functional in *Bacillus subtilis* and the cat gene conferring chloramphenicol resistance.

Variant BM4 (F290E) was constructed using the megaprimer approach (Sarkar and Sommer, 1990) with plasmid pTVB191 as template.

Primer p1 (SEQ ID NO: 52) and mutagenic oligonucleotide bm4 (SEQ ID NO: 47) were used to amplify a 444 bp fragment with polymerase chain reaction (PCR) under standard conditions. This fragment was purified from an agarose gel and used as 'Megaprimer' in a second PCR with primer p2 (SEQ ID NO: 53) resulting in a 531 bp fragment. This fragment was digested with restriction endonucleases HinDIII and Tth111I. The 389 bp fragment produced by this was ligated into plasmid pTVB191 that had been cleaved with the same two enzymes. The resulting plasmid was transformed into B. subtilis SHA273. Chloramphenicol resistant clones were selected by growing the transformants on plates containing chloramphenicol as well as insoluble starch. Clones expressing an active $\alpha$-amylase were isolated by selecting clones that formed halos after staining the plates with iodine vapour. The identity of the introduced mutations was confirmed by DNA sequencing.

Variants BM5(F290K), BM6(F290A), BM8(Q360E) and BM11(N102D) were constructed in a similar way. Details of their construction are given below.

Variant: BM5(F290K)
  mutagenic oligonucleotide: bm5 (SEQ ID NO: 48)
  Primer (1st PCR): p1 (SEQ ID NO: 52)
  Size of resulting fragment: 444 bp
  Primer (2nd PCR): p2 (SEQ ID NO: 53)
  Restriction endonucleases: HinDIII, Tth111I
  Size of cleaved fragment: 389 bp
Variant: BM6(F290A)
  mutagenic oligonucleotide: bm6 (SEQ ID NO: 49)
  Primer (1st PCR): p1 (SEQ ID NO: 52)
  Size of resulting fragment: 444 bp
  Primer (2nd PCR): p2 (SEQ ID NO: 53)
  Restriction endonucleases: HinDIII, Tth111I
  Size of cleaved fragment: 389 bp
Variant: BM8(Q360E)
  mutagenic oligonucleotide: bm8 (SEQ ID NO: 50)
  Primer (1st PCR): p1 (SEQ ID NO: 52)
  Size of resulting fragment: 230 bp
  Primer (2nd PCR): p2 (SEQ ID NO: 53) Restriction endonucleases: HinDIII, Tth111I
  Size of cleaved fragment: 389 bp
Variant: BM11(N102D)
  mutagenic oligonucleotide: bm11 (SEQ ID NO: 51)
  Primer (1st PCR): p3 (SEQ ID NO: 54)
  Size of resulting fragment: 577
  Primer (2nd PCR): p4 (SEQ ID NO: 55)
  Restriction endonucleases: HinDIII, PvuI
  Size of cleaved fragment: 576
Mutagenic oligonucleotides:
  bm4 (SEQ ID NO: 47): F290E
  primer 5'GTG TTT GAC GTC CCG CTT CAT GAG AAT TTA CAG G
  bm5 (SEQ ID NO: 48): F290K
  primer 5'GTG TTT GAC GTC CCG CTT CAT AAG AAT TTA CAG G
  bm6 (SEQ ID NO: 49): F290A
  primer 5'GTG TTT GAC GTC CCG CTT CAT GCC AAT TTA CAG G
  bm8 (SEQ ID NO: 50): Q360E
  primer 5'AGG GAA TCC GGA TAC CCT GAG GTT TTC TAC GG
  bm11 (SEQ ID NO: 51): N102D
  primer 5'GAT GTG GTT TTG GAT CAT AAG GCC GGC GCT GAT G
Other primers:
  p1: 5' CTG TTA TTA ATG CCG CCA AAC C (SEQ ID NO: 52)
  p2: 5' G GAA AAG AAA TGT TTA CGG TTG CG (SEQ ID NO: 53)
  p3: 5' G AAA TGA AGC GGA ACA TCA AAC ACG (SEQ ID NO: 54)
  p4: 5' GTA TGA TTT AGG AGA ATT CC (SEQ ID NO: 55)

Example 11

$\alpha$-Amylase activity at alkaline pH of variants of parent BAN:1–300/Termamyl:301–483 hybrid $\alpha$-amylase.

The measurements were made using solutions for the respective enzymes and utilizing the Phadebas assay (described above). The activity was measured after incubating for 15 minutes at 30° C. in 50 mM Britton-Robinson buffer adjusted to the indicated pH by NaOH.

NU/mg enzyme

| pH | wt | Q360E | F290A | F290K | F290E | N102D |
|---|---|---|---|---|---|---|
| 8.0 | 5300 | 7800 | 8300 | 4200 | 6600 | 6200 |
| 9.0 | 1600 | 2700 | 3400 | 2100 | 1900 | 1900 |

REFERENCES CITED

Klein, C., et al., *Biochemistry* 1992, 31, 8740–8746,

Mizuno, H., et al., *J. Mol. Biol.* (1993) 234, 1282–1283,

Chang, C., et al, *J. Mol. Biol.* (1993) 229, 235–238,

Larson, S. B., *J. Mol. Biol.* (1994) 235, 1560–1584,

Lawson, C. L., *J. Mol. Biol.* (1994) 236, 590–600,

Qian, M., et al., *J. Mol. Biol.* (1993) 231, 785–799,

Brady, R. L., et al., Acta Crystallogr. sect. B. 47, 527–535,

Swift, H. J., et al., Acta Crystallogr. sect. B. 47, 535-S44

A. Kadziola, Ph.D. Thesis: "An alpha-amylase from Barley and its Complex with a Substrate Analogue Inhibitor Studied by X-ray Crystallography", Department of Chemistry University of Copenhagen 1993

MacGregor, E. A., Food Hydrocolloids, 1987, Vol.1, No. 5–6, p. B. Diderichsen and L. Christiansen, Cloning of a maltogenic $\alpha$-amylase from *Bacillus stearothermophilus*, FEMS Microbiol. letters: 56: pp. 53–60 (1988)

Hudson et al., Practical Immunology, Third edition (1989), Blackwell Scientific Publications, Sambrook et al., *Molecular Cloning: A Laboratory Manual*, 2nd Ed., Cold Spring Harbor, 1989

S. L. Beaucage and M. H. Caruthers, *Tetrahedron Letters* 22, 1981, pp. 1859–1869

Matthes et al., *The EMBO J.* 3, 1984, pp. 801–805.

R. K. Saiki et al., *Science* 239, 1988, pp. 487–491.

Morinaga et al., (1984, Biotechnology 2:646–639)

Nelson and Long, *Analytical Biochemistry* 180, 1989, pp. 147–151 Hunkapiller et al., 1984, Nature 310:105–111

R. Higuchi, B. Krummel, and R. K. Saiki (1988). A general method of in vitro preparation and specific mutagenesis of DNA fragments: study of protein and DNA interactions. *Nucl. Acids Res.* 16:7351–7367.

Dubnau et al., 1971, *J. Mol. Biol.* 56, pp. 209–221.

Gryczan et al., 1978, *J. Bacteriol.* 134, pp. 318–329.

S. D. Erlich, 1977, *Proc. Natl. Acad. Sci.* 74, pp. 1680–1682.

Boel et al., 1990, *Biochemistry* 29, pp. 6244–6249.

What is claimed is:

1. A variant of a parent Termamyl-like α-amylase, wherein said variant has α-amylase activity and at least 80% sequence identity to said parent α-amylase and comprises one or more mutations at a position corresponding to a position in the amino acid sequence shown in SEQ ID NO: 2 selected from the group consisting of:
   T461P;
   Q174*;
   R181Q,N,S; and
   G182T,S,N.

2. The variant according to claim 1, wherein the variant further has one or more of the following substitutions or deletions:
   K142R;
   S193P;
   N195F;
   K269R,Q,
   N270Y,R,D;
   K311R;
   E346Q;
   K385R;
   K458R;
   P459T;
   D183*;
   G184*;
   K185A,R,D,C,E,Q,G,H,I,L,M,N,F,P,S,T,W,Y,V;
   A186T,S,N,I,V,R; and
   W189T,S,N,Q.

3. The variant according to claim 1, wherein said variant exhibits improved stability at pH 8 to 10.5 as compared to said parent α-amylase.

4. The variant according to claim 1, wherein said variant exhibits improved $Ca^{2+}$ stability at pH 8 to 10.5 as compared to said parent α-amylase.

5. The variant according to claim 1, wherein the parent Termamyl-like α-amylase is selected from the group consisting of:
   (i) Bacillus strain NCIB 12512 α-amylase having the sequence shown in SEQ ID NO: 1;
   (ii) *B. amyloliquefaciens α-amylase having the sequence shown in SEQ ID NO: 5;* and
   (iii) *B. licheniformis α-amylase having the sequence shown in SEQ ID NO: 4.*

6. The variant according to claim 1, wherein said variant exhibits increased specific activity at a temperature from 10 to 60° C. as compared to said parent α-amylase.

7. The variant according to claim 1, wherein said variant exhibits increased specific activity at a temperature from 20–50° C. as compared to said parent α-amylase.

8. The variant according to claim 1, wherein said variant exhibits increased specific activity at a temperature from 30–40° C. as compared to said parent α-amylase.

9. A detergent additive comprising an α-amylase variant according to claim 1.

10. The detergent additive of claim 9, wherein said additive is in the form of a non-dusting granulate, stabilized liquid or protected enzyme.

11. A detergent composition comprising an α-amylase variant according to claim 1.

12. A manual or automatic dishwashing detergent composition comprising an α-amylase variant according to claim 1.

13. A dishwashing detergent composition according to claim 12 further comprising an enzyme selected from the group consisting of a protease, a lipase, a peroxidase, another amylolytic enzyme and a cellulase.

14. A manual or automatic laundry washing composition comprising an α-amylase variant according to claim 1.

15. The variant according to claim 1, wherein the variant further comprises a deletion of amino acids at positions corresponding to D183 or G184 in the amino acid sequence shown in SEQ ID NO:2.

16. The variant according to claim 1, wherein the variant further comprises a mutation of S193P in the amino acid sequence shown in SEQ ID NO: 2.

17. The variant according to claim 1, wherein the variant further comprises a mutation of N195F in the amino acid sequence shown in SEQ ID NO: 2.

18. The variant according to claim 1, wherein the variant further comprises a mutation of K385R in the amino acid sequence shown in SEQ ID NO: 2.

19. The variant according to claim 1, wherein the variant comprises a mutation of T461P in the amino acid sequence shown in SEQ ID NO: 2.

20. The variant according to claim 1, wherein the variant comprises a deletion of Q174 in the amino acid sequence shown in SEQ ID NO: 2.

21. The variant according to claim 1, wherein the variant comprises a mutation of R181Q,N,S in the amino acid sequence shown in SEQ ID NO: 2.

22. The variant according to claim 1, wherein the variant comprises a mutation of G182T,S,N in the amino acid sequence shown in SEQ ID NO: 2.

23. The variant according to claim 1, wherein the variant further comprises a mutation of K142R in the amino acid sequence shown in SEQ ID NO: 2.

24. The variant according to claim 1, wherein the variant further comprises a mutation of K269R,Q in the amino acid sequence shown in SEQ ID NO: 2.

25. The variant according to claim 1, wherein the variant further comprises a mutation of N270Y,R,D in the amino acid sequence shown in SEQ ID NO: 2.

26. The variant according to claim 1, wherein the variant further comprises a mutation of K311R in the amino acid sequence shown in SEQ ID NO: 2.

27. The variant according to claim 1, wherein the variant further comprises a mutation of E346Q in the amino acid sequence shown in SEQ ID NO: 2.

28. The variant according to claim 1, wherein the variant further comprises a mutation of K458R in the amino acid sequence shown in SEQ ID NO: 2.

29. The variant according to claim 1, wherein the variant further comprises a mutation of P459T in the amino acid sequence shown in SEQ ID NO: 2.

30. The variant according to claim 1, wherein the variant further comprises a mutation of D183 in the amino acid sequence shown in SEQ ID NO: 2.

31. The variant according to claim 1, wherein the variant further comprises a mutation of G184* in the amino acid sequence shown in SEQ ID NO: 2.

32. The variant according to claim 1, wherein the variant further comprises a mutation of K185A,R,D,C,E,Q,G,H,I,L,M,N,F,P,S,T,W,Y,V in the amino acid sequence shown in SEQ ID NO: 2.

33. The variant according to claim 1, wherein the variant further comprises a mutation of A186T,S,N,I,V,R in the amino acid sequence shown in SEQ ID NO: 2.

34. The variant according to claim 1, wherein the variant further comprises a mutation of W189T,S,N,Q in the amino acid sequence shown in SEQ ID NO: 2.

* * * * *

SEQUENCE LISTING

<160> NUMBER OF SEQ ID NOS: 58

<210> SEQ ID NO 1
<211> LENGTH: 485
<212> TYPE: PRT
<213> ORGANISM: Bacillus

<400> SEQUENCE: 1

```
His His Asn Gly Thr Asn Gly Thr Met Met Gln Tyr Phe Glu Trp Tyr
  1               5                  10                  15

Leu Pro Asn Asp Gly Asn His Trp Asn Arg Leu Arg Asp Asp Ala Ala
             20                  25                  30

Asn Leu Lys Ser Lys Gly Ile Thr Ala Val Trp Ile Pro Pro Ala Trp
         35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Asn Gln Leu Gln Ala Ala Val Thr Ser Leu Lys Asn Asn Gly
                 85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
```

-continued

```
                355                 360                 365
Gly Asp Tyr Tyr Gly Ile Pro Thr His Gly Val Pro Ala Met Lys Ser
            370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
            435                 440                 445

Gln Val Trp Arg Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240
```

-continued

```
Ile Lys Tyr Ser Phe Thr Arg Asp Trp Leu Thr His Val Arg Asn Ala
            245                 250                 255
Thr Gly Lys Glu Met Phe Ala Val Ala Glu Phe Trp Lys Asn Asp Leu
        260                 265                 270
Gly Ala Leu Glu Asn Tyr Leu Asn Lys Thr Asn Trp Asn His Ser Val
        275                 280                 285
Phe Asp Val Pro Leu His Tyr Asn Leu Tyr Asn Ala Ser Asn Ser Gly
        290                 295                 300
Gly Asn Tyr Asp Met Ala Lys Leu Leu Asn Gly Thr Val Val Gln Lys
305                 310                 315                 320
His Pro Met His Ala Val Thr Phe Val Asp Asn His Asp Ser Gln Pro
            325                 330                 335
Gly Glu Ser Leu Glu Ser Phe Val Gln Glu Trp Phe Lys Pro Leu Ala
            340                 345                 350
Tyr Ala Leu Ile Leu Thr Arg Glu Gln Gly Tyr Pro Ser Val Phe Tyr
            355                 360                 365
Gly Asp Tyr Tyr Gly Ile Pro Thr His Ser Val Pro Ala Met Lys Ala
        370                 375                 380
Lys Ile Asp Pro Ile Leu Glu Ala Arg Gln Asn Phe Ala Tyr Gly Thr
385                 390                 395                 400
Gln His Asp Tyr Phe Asp His His Asn Ile Ile Gly Trp Thr Arg Glu
                405                 410                 415
Gly Asn Thr Thr His Pro Asn Ser Gly Leu Ala Thr Ile Met Ser Asp
            420                 425                 430
Gly Pro Gly Gly Glu Lys Trp Met Tyr Val Gly Gln Asn Lys Ala Gly
        435                 440                 445
Gln Val Trp His Asp Ile Thr Gly Asn Lys Pro Gly Thr Val Thr Ile
        450                 455                 460
Asn Ala Asp Gly Trp Ala Asn Phe Ser Val Asn Gly Gly Ser Val Ser
465                 470                 475                 480
Ile Trp Val Lys Arg
                485

<210> SEQ ID NO 3
<211> LENGTH: 514
<212> TYPE: PRT
<213> ORGANISM: Bacillus stearothermophilus
<400> SEQUENCE: 3
Ala Ala Pro Phe Asn Gly Thr Met Met Gln Tyr Phe Glu Trp Tyr Leu
  1               5                  10                  15
Pro Asp Asp Gly Thr Leu Trp Thr Lys Val Ala Asn Glu Ala Asn Asn
            20                  25                  30
Leu Ser Ser Leu Gly Ile Thr Ala Leu Trp Leu Pro Pro Ala Tyr Lys
        35                  40                  45
Gly Thr Ser Arg Ser Asp Val Gly Tyr Gly Val Tyr Asp Leu Tyr Asp
    50                  55                  60
Leu Gly Glu Phe Asn Gln Lys Gly Ala Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asp His Lys Gly Gly Ala Asp Gly
            100                 105                 110
Thr Glu Trp Val Asp Ala Val Glu Val Asn Pro Ser Asp Arg Asn Gln
        115                 120                 125
```

-continued

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 4
<211> LENGTH: 483
<212> TYPE: PRT
<213> ORGANISM: Bacillus licheniformis

<400> SEQUENCE: 4

```
Ala Asn Leu Asn Gly Thr Leu Met Gln Tyr Phe Glu Trp Tyr Met Pro
  1               5                  10                  15
Asn Asp Gly Gln His Trp Arg Arg Leu Gln Asn Asp Ser Ala Tyr Leu
             20                  25                  30
Ala Glu His Gly Ile Thr Ala Val Trp Ile Pro Pro Ala Tyr Lys Gly
         35                  40                  45
Thr Ser Gln Ala Asp Val Gly Tyr Gly Ala Tyr Asp Leu Tyr Asp Leu
     50                  55                  60
Gly Glu Phe His Gln Lys Gly Thr Val Arg Thr Lys Tyr Gly Thr Lys
 65                  70                  75                  80
Gly Glu Leu Gln Ser Ala Ile Lys Ser Leu His Ser Arg Asp Ile Asn
                 85                  90                  95
Val Tyr Gly Asp Val Val Ile Asn His Lys Gly Gly Ala Asp Ala Thr
            100                 105                 110
Glu Asp Val Thr Ala Val Glu Val Asp Pro Ala Asp Arg Asn Arg Val
        115                 120                 125
Ile Ser Gly Glu His Leu Ile Lys Ala Trp Thr His Phe His Phe Pro
130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
            180                 185                 190
Tyr Asp Tyr Leu Met Tyr Ala Asp Ile Asp Tyr Asp His Pro Asp Val
        195                 200                 205
Ala Ala Glu Ile Lys Arg Trp Gly Thr Trp Tyr Ala Asn Glu Leu Gln
    210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
            260                 265                 270
Tyr Leu Asn Lys Thr Asn Phe Asn His Ser Val Phe Asp Val Pro Leu
        275                 280                 285
His Tyr Gln Phe His Ala Ala Ser Thr Gln Gly Gly Tyr Asp Met
    290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Asp Ser Gln Arg Glu Ile Pro Ala Leu Lys His Lys Ile
    370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
```

```
                         405                 410                 415
Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 5
<211> LENGTH: 480
<212> TYPE: PRT
<213> ORGANISM: Bacillus amyloliqufaciens

<400> SEQUENCE: 5

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
```

```
                    290                 295                 300
Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Thr Ser Pro Lys Glu Ile Pro Ser Leu Lys Asp Asn Ile
                370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
                420                 425                 430

Gly Gly Ser Lys Arg Met Tyr Ala Gly Leu Lys Asn Ala Gly Glu Thr
                435                 440                 445

Trp Tyr Asp Ile Thr Gly Asn Arg Ser Asp Thr Val Lys Ile Gly Ser
                450                 455                 460

Asp Gly Trp Gly Glu Phe His Val Asn Asp Gly Ser Val Ser Ile Tyr
465                 470                 475                 480

<210> SEQ ID NO 6
<211> LENGTH: 485
<212> TYPE: PRT
<213> ORGANISM: Bacillus sp.

<400> SEQUENCE: 6

His His Asn Gly Thr Asn Gly Thr Met Met Gln Tyr Phe Glu Trp Tyr
  1               5                  10                  15

Leu Pro Asn Asp Gly Asn His Trp Asn Arg Leu Asn Ser Asp Ala Ser
                 20                  25                  30

Asn Leu Lys Ser Lys Gly Ile Thr Ala Val Trp Ile Pro Pro Ala Trp
             35                  40                  45

Lys Gly Ala Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Gln Ala Ala Val Thr Ser Leu Lys Asn Asn Gly
                 85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190
```

-continued

```
Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485
```

<210> SEQ ID NO 7
<211> LENGTH: 485
<212> TYPE: PRT
<213> ORGANISM: Bacillus sp.

<400> SEQUENCE: 7

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80
```

-continued

```
Thr Arg Asn Gln Leu Gln Ala Ala Val Thr Ser Leu Lys Asn Asn Gly
                 85                  90                  95
Ile Gln Val Tyr Gly Asp Val Val Met Asn His Lys Gly Gly Ala Asp
            100                 105                 110
Gly Thr Glu Ile Val Asn Ala Val Glu Val Asn Arg Ser Asn Arg Asn
        115                 120                 125
Gln Glu Thr Ser Gly Glu Tyr Ala Ile Glu Ala Trp Thr Lys Phe Asp
    130                 135                 140
Phe Pro Gly Arg Gly Asn Asn His Ser Ser Phe Lys Trp Arg Trp Tyr
145                 150                 155                 160
His Phe Asp Gly Thr Asp Trp Asp Gln Ser Arg Gln Leu Gln Asn Lys
                165                 170                 175
Ile Tyr Lys Phe Arg Gly Thr Gly Lys Ala Trp Asp Trp Glu Val Asp
            180                 185                 190
Thr Glu Asn Gly Asn Tyr Asp Tyr Leu Met Tyr Ala Asp Val Asp Met
        195                 200                 205
Asp His Pro Glu Val Ile His Glu Leu Arg Asn Trp Gly Val Trp Tyr
    210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Thr
                245                 250                 255
Thr Gly Lys Pro Met Phe Ala Val Ala Glu Phe Trp Lys Asn Asp Leu
            260                 265                 270
Gly Ala Ile Glu Asn Tyr Leu Asn Lys Thr Ser Trp Asn His Ser Val
        275                 280                 285
Phe Asp Val Pro Leu His Tyr Asn Leu Tyr Asn Ala Ser Asn Ser Gly
    290                 295                 300
Gly Tyr Tyr Asp Met Arg Asn Ile Leu Asn Gly Ser Val Val Gln Lys
305                 310                 315                 320
His Pro Thr His Ala Val Thr Phe Val Asp Asn His Asp Ser Gln Pro
                325                 330                 335
Gly Glu Ala Leu Glu Ser Phe Val Gln Gln Trp Phe Lys Pro Leu Ala
            340                 345                 350
Tyr Ala Leu Val Leu Thr Arg Glu Gln Gly Tyr Pro Ser Val Phe Tyr
        355                 360                 365
Gly Asp Tyr Tyr Gly Ile Pro Thr His Gly Val Pro Ala Met Lys Ser
    370                 375                 380
Lys Ile Asp Pro Leu Leu Gln Ala Arg Gln Thr Phe Ala Tyr Gly Thr
385                 390                 395                 400
Gln His Asp Tyr Phe Asp His His Asp Ile Ile Gly Trp Thr Arg Glu
                405                 410                 415
Gly Asn Ser Ser His Pro Asn Ser Gly Leu Ala Thr Ile Met Ser Asp
            420                 425                 430
Gly Pro Gly Gly Asn Lys Trp Met Tyr Val Gly Lys Asn Lys Ala Gly
        435                 440                 445
Gln Val Trp Arg Asp Ile Thr Gly Asn Arg Thr Gly Thr Val Thr Ile
    450                 455                 460
Asn Ala Asp Gly Trp Gly Asn Phe Ser Val Asn Gly Gly Ser Val Ser
465                 470                 475                 480
Val Trp Val Lys Gln
                485
```

```
<210> SEQ ID NO 8
<211> LENGTH: 485
<212> TYPE: PRT
<213> ORGANISM: Bacillus sp.

<400> SEQUENCE: 8

His His Asn Gly Thr Asn Gly Thr Met Met Gln Tyr Phe Glu Trp His
  1               5                  10                  15

Leu Pro Asn Asp Gly Asn His Trp Asn Arg Leu Arg Asp Asp Ala Ser
             20                  25                  30

Asn Leu Arg Asn Arg Gly Ile Thr Ala Ile Trp Ile Pro Pro Ala Trp
         35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
        130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
370                 375                 380
```

```
Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
            405                 410                 415

Gly Asn Thr Thr His Pro Asn Ser Gly Leu Ala Thr Ile Met Ser Asp
        420                 425                 430

Gly Pro Gly Gly Glu Lys Trp Met Tyr Val Gly Gln Asn Lys Ala Gly
    435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
            485
```

<210> SEQ ID NO 9
<211> LENGTH: 1455
<212> TYPE: DNA
<213> ORGANISM: Bacillus

<400> SEQUENCE: 9

```
catcataatg gaacaaatgg tactatgatg caatatttcg aatggtattt gccaaatgac    60
gggaatcatt ggaacaggtt gagggatgac gcagctaact taaagagtaa agggataaca   120
gctgtatgga tcccacctgc atggaagggg acttcccaga tgatgtaggt tatggagcc    180
tatgatttat atgatcttgg agagtttaac cagaagggga cggttcgtac aaaatatgga   240
acacgcaacc agctacaggc tgcggtgacc tctttaaaaa ataacggcat tcaggtatat   300
ggtgatgtcg tcatgaatca taaaggtgga gcagatggta cggaaattgt aaatgcggta   360
gaagtgaatc ggagcaaccg aaaccaggaa acctcaggag agtatgcaat agaagcgtgg   420
acaaagtttg attttcctgg aagaggaaat aaccattcca gctttaagtg gcgctggtat   480
cattttgatg gacagattg ggatcagtca cgccagcttc aaaacaaaat atataaattc   540
agggaacag gcaaggcctg ggactgggaa gtcgatacag agaatggcaa ctatgactat   600
cttatgtatg cagacgtgga tatggatcac ccagaagtaa tacatgaact tagaaactgg   660
ggagtgtggt atacgaatac actgaacctt gatggattta aatagatgc agtgaaacat   720
ataaaatata gctttacgag agattggctt acacatgtgc gtaacaccac aggtaaacca   780
atgtttgcag tggctgagtt ttggaaaaat gaccttggtg caattgaaaa ctatttgaat   840
aaaacaagtt ggaatcactc ggtgtttgat gttcctctcc actataattt gtacaatgca   900
tctaatagcg gtggttatta tgatatgaga atatattttaa atggttctgt ggtgcaaaaa   960
catccaacac atgccgttac ttttgttgat aaccatgatt ctcagcccgg ggaagcattg  1020
gaatcctttg ttcaacaatg gtttaaacca cttgcatatg cattggttct gacaagggaa  1080
caaggttatc cttccgtatt ttatggggat tactacggta tcccaaccca tggtgttccg  1140
gctatgaaat ctaaaataga ccctcttctg caggcacgtc aaacttttgc ctatggtacg  1200
cagcatgatt actttgatca tcatgatatt atcggttgga caagagaggg aaatagctcc  1260
catccaaatt caggccttgc caccattatg tcagatggtc caggtggtaa caatggatg  1320
tatgtgggga aaaataaagc gggacaagtt tggagagata ttaccggaaa taggacaggc  1380
accgtcacaa ttaatgcaga cggatggggt aatttctctg ttaatggagg gtccgtttcg  1440
gtttgggtga agcaa                                                  1455
```

<210> SEQ ID NO 10
<211> LENGTH: 1455
<212> TYPE: DNA
<213> ORGANISM: Bacillus sp.

<400> SEQUENCE: 10

| | | | | | |
|---|---|---|---|---|---|
| catcataatg | ggacaaatgg | gacgatgatg | caatactttg | aatggcactt | gcctaatgat | 60 |
| gggaatcact | ggaatagatt | aagagatgat | gctagtaatc | taagaaatag | aggtataacc | 120 |
| gctatttgga | ttccgcctgc | ctggaaaggg | acttcgcaaa | atgatgtggg | gtatggagcc | 180 |
| tatgatcttt | atgatttagg | ggaatttaat | caaaagggga | cggttcgtac | taagtatggg | 240 |
| acacgtagtc | aattggagtc | tgccatccat | gctttaaaga | ataatggcgt | tcaagtttat | 300 |
| ggggatgtag | tgatgaacca | taaaggagga | gctgatgcta | cagaaaacgt | tcttgctgtc | 360 |
| gaggtgaatc | caaataaccg | gaatcaagaa | atatctgggg | actacacaat | tgaggcttgg | 420 |
| actaagtttg | attttccagg | gagggtaat | acatactcag | actttaaatg | gcgttggtat | 480 |
| catttcgatg | tgtagattg | ggatcaatca | cgacaattcc | aaaatcgtat | ctacaaattc | 540 |
| cgaggtgatg | gtaaggcatg | ggattgggaa | gtagattcgg | aaaatggaaa | ttatgattat | 600 |
| ttaatgtatg | cagatgtaga | tatggatcat | ccggaggtag | taaatgagct | tagaagatgg | 660 |
| ggagaatggt | atacaaatac | attaaatctt | gatggattta | ggatcgatgc | ggtgaagcat | 720 |
| attaaatata | gctttacacg | tgattggttg | acccatgtaa | gaaacgcaac | gggaaaagaa | 780 |
| atgtttgctg | ttgctgaatt | ttggaaaaat | gatttaggtg | ccttggagaa | ctatttaaat | 840 |
| aaaacaaact | ggaatcattc | tgtctttgat | gtccccttc | attataatct | ttataacgcg | 900 |
| tcaaatagtg | gaggcaacta | tgacatggca | aaacttctta | atggaacggt | tgttcaaaag | 960 |
| catccaatgc | atgccgtaac | ttttgtggat | aatcacgatt | ctcaacctgg | ggaatcatta | 1020 |
| gaatcatttg | tacaagaatg | gtttaagcca | cttgcttatg | cgcttatttt | aacaagagaa | 1080 |
| caaggctatc | cctctgtctt | ctatggtgac | tactatggaa | ttccaacaca | tagtgtccca | 1140 |
| gcaatgaaag | ccaagattga | tccaatctta | gaggcgcgtc | aaaattttgc | atatggaaca | 1200 |
| caacatgatt | attttgacca | tcataatata | atcggatgga | cacgtgaagg | aaataccacg | 1260 |
| catcccaatt | caggacttgc | gactatcatg | tcggatgggc | caggggaga | gaaatggatg | 1320 |
| tacgtagggc | aaaataaagc | aggtcaagtt | tggcatgaca | taactggaaa | taaaccagga | 1380 |
| acagttacga | tcaatgcaga | tggatgggct | aattttcag | taaatggagg | atctgtttcc | 1440 |
| atttgggtga | aacga | | | | | 1455 |

<210> SEQ ID NO 11
<211> LENGTH: 1548
<212> TYPE: DNA
<213> ORGANISM: Bacillus stearothermophilus

<400> SEQUENCE: 11

| | | | | | |
|---|---|---|---|---|---|
| gccgcaccgt | taacggcac | catgatgcag | tattttgaat | ggtacttgcc | ggatgatggc | 60 |
| acgttatgga | ccaaagtggc | caatgaagcc | aacaacttat | ccagccttgg | catcaccgct | 120 |
| ctttggctgc | cgcccgctta | caaggaaca | agccgcagcg | acgtaggta | cggagtatac | 180 |
| gacttgtatg | acctcggcga | attcaatcaa | aagggaccg | tccgcacaaa | atacggaaca | 240 |
| aaagctcaat | atcttcaagc | cattcaagcc | gcccacgccg | ctggaatgca | agtgtacgcc | 300 |
| gatgtcgtgt | tcgaccataa | aggcggcgct | gacggcacgg | aatgggtgga | cgccgtcgaa | 360 |

-continued

```
gtcaatccgt ccgaccgcaa ccaagaaatc tcgggcacct atcaaatcca agcatggacg      420
aaatttgatt ttcccgggcg gggcaacacc tactccagct ttaagtggcg ctggtaccat      480
tttgacggcg ttgattggga cgaaagccga aaattgagcc gcatttacaa attccgcggc      540
atcggcaaag cgtgggattg ggaagtagac acggaaaacg gaaactatga ctacttaatg      600
tatgccgacc ttgatatgga tcatcccgaa gtcgtgaccg agctgaaaaa ctgggggaaa      660
tggtatgtca acacaacgaa cattgatggg ttccggcttg atgccgtcaa gcatattaag      720
ttcagttttt ttcctgattg gttgtcgtat gtgcgttctc agactggcaa gccgctattt      780
accgtcgggg aatattggag ctatgacatc aacaagttgc acaattacat tacgaaaaca      840
gacggaacga tgtctttgtt tgatgccccg ttacacaaca aattttatac cgcttccaaa      900 tcaggggggcg catttgatat gcgcacgtta atgaccaata ctctcatgaa agatcaaccg      960
acattggccc tcaccttcgt tgataatcat gacaccgaac ccggccaagc gctgcagtca     1020
tgggtcgacc catggttcaa accgttggct tacgccttta ttctaactcg gcaggaagga     1080
tacccgtgcg tctttatgg tgactattat ggcattccac aatataacat tccttcgctg     1140
aaaagcaaaa tcgatccgct cctcatcgcg cgcagggatt atgcttacgg aacgcaacat     1200
gattatcttg atcactccga catcatcggg tggacaaggg aaggggcac tgaaaaacca     1260 ggatccggac tggccgcact gatcaccgat gggccggag gaagcaaatg gatgtacgtt     1320
ggcaaacaac acgctggaaa agtgttctat gaccttaccg gcaaccggag tgacaccgtc     1380
accatcaaca gtgatggatg ggggaattc aaagtcaatg gcggttcggt ttcggtttgg     1440
gttcctagaa aaacgaccgt ttctaccatc gctcggccga tcacaacccg accgtggact     1500
ggtgaattcg tccgttggac cgaaccacgg ttggtggcat ggccttga                 1548
```

<210> SEQ ID NO 12
<211> LENGTH: 1920
<212> TYPE: DNA
<213> ORGANISM: Bacillus licheniformis
<220> FEATURE:
<221> NAME/KEY: CDS
<222> LOCATION: (421)...(1872)

<400> SEQUENCE: 12

```
cggaagattg gaagtacaaa aataagcaaa agattgtcaa tcatgtcatg agccatgcgg       60
gagacggaaa aatcgtctta atgcacgata tttatgcaac gttcgcagat gctgctgaag      120
agattattaa aaagctgaaa gcaaaaggct atcaattggt aactgtatct cagcttgaag      180
aagtgaagaa gcagagaggc tattgaataa atgagtagaa gcgccatatc ggcgcttttc      240
ttttggaaga aaatataggg aaaatggtac ttgttaaaaa ttcggaatat ttatacaaca      300
tcatatgttt cacattgaaa ggggaggaga atcatgaaac aacaaaaacg gctttacgcc      360
cgattgctga cgctgttatt tgcgctcatc ttcttgctgc ctcattctgc agcagcggcg      420 gca aat ctt aat ggg acg ctg atg cag tat ttt gaa tgg tac atg ccc       468
Ala Asn Leu Asn Gly Thr Leu Met Gln Tyr Phe Glu Trp Tyr et Pro
  1               5                  10                  15 aat gac ggc caa cat tgg agg cgt ttg caa aac gac tcg gca tat ttg      516
Asn Asp Gly Gln His Trp Arg Arg Leu Gln Asn Asp Ser Ala Tyr Leu
              20                  25                  30 gct gaa cac ggt att act gcc gtc tgg att ccc ccg gca tat aag gga      564
Ala Glu His Gly Ile Thr Ala Val Trp Ile Pro Pro Ala Tyr Lys Gly
          35                  40                  45
```

|   |   |   |   |   |   |   |   |   |   |   |   |   |   |   |   |   |
|---|---|---|---|---|---|---|---|---|---|---|---|---|---|---|---|---|
| acg | agc | caa | gcg | gat | gtg | ggc | tac | ggt | gct | tac | gac | ctt | tat | gat | tta | 612 |
| Thr | Ser | Gln | Ala | Asp | Val | Gly | Tyr | Gly | Ala | Tyr | Asp | Leu | Tyr | Asp | Leu | |
| | 50 | | | | 55 | | | | | 60 | | | | | | |
| ggg | gag | ttt | cat | caa | aaa | ggg | acg | gtt | cgg | aca | aag | tac | ggc | aca | aaa | 660 |
| Gly | Glu | Phe | His | Gln | Lys | Gly | Thr | Val | Arg | Thr | Lys | Tyr | Gly | Thr | Lys | |
| 65 | | | | | 70 | | | | | 75 | | | | | 80 | |
| gga | gag | ctg | caa | tct | gcg | atc | aaa | agt | ctt | cat | tcc | cgc | gac | att | aac | 708 |
| Gly | Glu | Leu | Gln | Ser | Ala | Ile | Lys | Ser | Leu | His | Ser | Arg | Asp | Ile | Asn | |
| | | | | 85 | | | | | 90 | | | | | 95 | | |
| gtt | tac | ggg | gat | gtg | gtc | atc | aac | cac | aaa | ggc | ggc | gct | gat | gcg | acc | 756 |
| Val | Tyr | Gly | Asp | Val | Val | Ile | Asn | His | Lys | Gly | Gly | Ala | Asp | Ala | Thr | |
| | | | 100 | | | | | 105 | | | | | 110 | | | |
| gaa | gat | gta | acc | gcg | gtt | gaa | gtc | gat | ccc | gct | gac | cgc | aac | cgc | gta | 804 |
| Glu | Asp | Val | Thr | Ala | Val | Glu | Val | Asp | Pro | Ala | Asp | Arg | Asn | Arg | Val | |
| | | | 115 | | | | | 120 | | | | | 125 | | | |
| att | tca | gga | gaa | cac | cta | att | aaa | gcc | tgg | aca | cat | ttt | cat | ttt | ccg | 852 |
| Ile | Ser | Gly | Glu | His | Leu | Ile | Lys | Ala | Trp | Thr | His | Phe | His | Phe | Pro | |
| | 130 | | | | | 135 | | | | | 140 | | | | | |
| ggg | cgc | ggc | agc | aca | tac | agc | gat | ttt | aaa | tgg | cat | tgg | tac | cat | ttt | 900 |
| Gly | Arg | Gly | Ser | Thr | Tyr | Ser | Asp | Phe | Lys | Trp | His | Trp | Tyr | His | Phe | |
| 145 | | | | | 150 | | | | | 155 | | | | | 160 | |
| gac | gga | acc | gat | tgg | gac | gag | tcc | cga | aag | ctg | aac | cgc | atc | tat | aag | 948 |
| Asp | Gly | Thr | Asp | Trp | Asp | Glu | Ser | Arg | Lys | Leu | Asn | Arg | Ile | Tyr | Lys | |
| | | | 165 | | | | | 170 | | | | | 175 | | | |
| ttt | caa | gga | aag | gct | tgg | gat | tgg | gaa | gtt | tcc | aat | gaa | aac | ggc | aac | 996 |
| Phe | Gln | Gly | Lys | Ala | Trp | Asp | Trp | Glu | Val | Ser | Asn | Glu | Asn | Gly | Asn | |
| | | | 180 | | | | | 185 | | | | | 190 | | | |
| tat | gat | tat | ttg | atg | tat | gcc | gac | atc | gat | tat | gac | cat | cct | gat | gtc | 1044 |
| Tyr | Asp | Tyr | Leu | Met | Tyr | Ala | Asp | Ile | Asp | Tyr | Asp | His | Pro | Asp | Val | |
| | | | 195 | | | | | 200 | | | | | 205 | | | |
| gca | gca | gaa | att | aag | aga | tgg | ggc | act | tgg | tat | gcc | aat | gaa | ctg | caa | 1092 |
| Ala | Ala | Glu | Ile | Lys | Arg | Trp | Gly | Thr | Trp | Tyr | Ala | Asn | Glu | Leu | Gln | |
| | | 210 | | | | | 215 | | | | | 220 | | | | |
| ttg | gac | ggt | ttc | cgt | ctt | gat | gct | gtc | aaa | cac | att | aaa | ttt | tct | ttt | 1140 |
| Leu | Asp | Gly | Phe | Arg | Leu | Asp | Ala | Val | Lys | His | Ile | Lys | Phe | Ser | Phe | |
| 225 | | | | | 230 | | | | | 235 | | | | | 240 | |
| ttg | cgg | gat | tgg | gtt | aat | cat | gtc | agg | gaa | aaa | acg | ggg | aag | gaa | atg | 1188 |
| Leu | Arg | Asp | Trp | Val | Asn | His | Val | Arg | Glu | Lys | Thr | Gly | Lys | Glu | Met | |
| | | | | 245 | | | | | 250 | | | | | 255 | | |
| ttt | acg | gta | gct | gaa | tat | tgg | cag | aat | gac | ttg | ggc | gcg | ctg | gaa | aac | 1236 |
| Phe | Thr | Val | Ala | Glu | Tyr | Trp | Gln | Asn | Asp | Leu | Gly | Ala | Leu | Glu | Asn | |
| | | | | 260 | | | | | 265 | | | | | 270 | | |
| tat | ttg | aac | aaa | aca | aat | ttt | aat | cat | tca | gtg | ttt | gac | gtg | ccg | ctt | 1284 |
| Tyr | Leu | Asn | Lys | Thr | Asn | Phe | Asn | His | Ser | Val | Phe | Asp | Val | Pro | Leu | |
| | | | 275 | | | | | 280 | | | | | 285 | | | |
| cat | tat | cag | ttc | cat | gct | gca | tcg | aca | cag | gga | ggc | ggc | tat | gat | atg | 1332 |
| His | Tyr | Gln | Phe | His | Ala | Ala | Ser | Thr | Gln | Gly | Gly | Gly | Tyr | Asp | Met | |
| | | 290 | | | | | 295 | | | | | 300 | | | | |
| agg | aaa | ttg | ctg | aac | ggt | acg | gtc | gtt | tcc | aag | cat | ccg | ttg | aaa | tcg | 1380 |
| Arg | Lys | Leu | Leu | Asn | Gly | Thr | Val | Val | Ser | Lys | His | Pro | Leu | Lys | Ser | |
| 305 | | | | | 310 | | | | | 315 | | | | | 320 | |
| gtt | aca | ttt | gtc | gat | aac | cat | gat | aca | cag | ccg | ggg | caa | tcg | ctt | gag | 1428 |
| Val | Thr | Phe | Val | Asp | Asn | His | Asp | Thr | Gln | Pro | Gly | Gln | Ser | Leu | Glu | |
| | | | | 325 | | | | | 330 | | | | | 335 | | |
| tcg | act | gtc | caa | aca | tgg | ttt | aag | ccg | ctt | gct | tac | gct | ttt | att | ctc | 1476 |
| Ser | Thr | Val | Gln | Thr | Trp | Phe | Lys | Pro | Leu | Ala | Tyr | Ala | Phe | Ile | Leu | |
| | | | 340 | | | | | 345 | | | | | 350 | | | |
| aca | agg | gaa | tct | gga | tac | cct | cag | gtt | ttc | tac | ggg | gat | atg | tac | ggg | 1524 |
| Thr | Arg | Glu | Ser | Gly | Tyr | Pro | Gln | Val | Phe | Tyr | Gly | Asp | Met | Tyr | Gly | |
| | | 355 | | | | | 360 | | | | | 365 | | | | |

| | | | | | | | | | | | | | | | | |
|---|---|---|---|---|---|---|---|---|---|---|---|---|---|---|---|---|
| acg | aaa | gga | gac | tcc | cag | cgc | gaa | att | cct | gcc | ttg | aaa | cac | aaa | att | 1572 |
| Thr | Lys | Gly | Asp | Ser | Gln | Arg | Glu | Ile | Pro | Ala | Leu | Lys | His | Lys | Ile | |
| | 370 | | | | 375 | | | | | 380 | | | | | | |
| gaa | ccg | atc | tta | aaa | gcg | aga | aaa | cag | tat | gcg | tac | gga | gca | cag | cat | 1620 |
| Glu | Pro | Ile | Leu | Lys | Ala | Arg | Lys | Gln | Tyr | Ala | Tyr | Gly | Ala | Gln | His | |
| 385 | | | | | 390 | | | | | 395 | | | | | 400 | |
| gat | tat | ttc | gac | cac | cat | gac | att | gtc | ggc | tgg | aca | agg | gaa | ggc | gac | 1668 |
| Asp | Tyr | Phe | Asp | His | His | Asp | Ile | Val | Gly | Trp | Thr | Arg | Glu | Gly | Asp | |
| | | | | 405 | | | | | 410 | | | | | 415 | | |
| agc | tcg | gtt | gca | aat | tca | ggt | ttg | gcg | gca | tta | ata | aca | gac | gga | ccc | 1716 |
| Ser | Ser | Val | Ala | Asn | Ser | Gly | Leu | Ala | Ala | Leu | Ile | Thr | Asp | Gly | Pro | |
| | | | 420 | | | | | 425 | | | | | 430 | | | |
| ggt | ggg | gca | aag | cga | atg | tat | gtc | ggc | cgg | caa | aac | gcc | ggt | gag | aca | 1764 |
| Gly | Gly | Ala | Lys | Arg | Met | Tyr | Val | Gly | Arg | Gln | Asn | Ala | Gly | Glu | Thr | |
| | | | | 435 | | | | | 440 | | | | | 445 | | |
| tgg | cat | gac | att | acc | gga | aac | cgt | tcg | gag | ccg | gtt | gtc | atc | aat | tcg | 1812 |
| Trp | His | Asp | Ile | Thr | Gly | Asn | Arg | Ser | Glu | Pro | Val | Val | Ile | Asn | Ser | |
| | | | 450 | | | | | 455 | | | | | 460 | | | |
| gaa | ggc | tgg | gga | gag | ttt | cac | gta | aac | ggc | ggg | tcg | gtt | tca | att | tat | 1860 |
| Glu | Gly | Trp | Gly | Glu | Phe | His | Val | Asn | Gly | Gly | Ser | Val | Ser | Ile | Tyr | |
| 465 | | | | | 470 | | | | | 475 | | | | | 480 | |
| gtt | caa | aga | tag | aagagcagag | | aggacggatt | | tcctgaagga | | aatccgtttt | | | | | | 1912 |
| Val | Gln | Arg | * | | | | | | | | | | | | | |
| tttattttt | | | | | | | | | | | | | | | | 1920 |

```
<210> SEQ ID NO 13
<211> LENGTH: 1455
<212> TYPE: DNA
<213> ORGANISM: Bacillus sp.

<400> SEQUENCE: 13
```

| | | | | | |
|---|---|---|---|---|---|
| catcataatg | gaacaaatgg | tactatgatg | caatatttcg | aatggtattt | gccaaatgac | 60 |
| gggaatcatt | ggaacaggtt | gagggatgac | gcagctaact | taaagagtaa | agggataaca | 120 |
| gctgtatgga | tcccacctgc | atggaagggg | acttcccaga | atgatgtagg | ttatggagcc | 180 |
| tatgatttat | atgatcttgg | agagtttaac | cagaagggga | cggttcgtac | aaaatatgga | 240 |
| acacgcaacc | agctacaggc | tgcggtgacc | tcttttaaaa | ataacggcat | tcaggtatat | 300 |
| ggtgatgtcg | tcatgaatca | taaaggtgga | gcagatggta | cggaaattgt | aaatgcggta | 360 |
| gaagtgaatc | ggagcaaccg | aaaccaggaa | acctcaggag | agtatgcaat | agaagcgtgg | 420 |
| acaaagtttg | attttcctgg | aagaggaaat | aaccattcca | gctttaagtg | gcgctggtat | 480 |
| cattttgatg | ggacagattg | ggatcagtca | cgccagcttc | aaaacaaaat | atataaattc | 540 |
| aggggaacag | gcaaggcctg | ggactgggaa | gtcgatacag | agaatggcaa | ctatgactat | 600 |
| cttatgtatg | cagacgtgga | tatggatcac | ccagaagtaa | tacatgaact | tagaaactgg | 660 |
| ggagtgtggt | atacgaatac | actgaacctt | gatggattta | gaatagatgc | agtgaaacat | 720 |
| ataaaatata | gctttacgag | agattggctt | acacatgtgc | gtaacaccac | aggtaaacca | 780 |
| atgtttgcag | tggctgagtt | ttggaaaaat | gaccttggtg | caattgaaaa | ctatttgaat | 840 |
| aaaacaagtt | ggaatcactc | ggtgtttgat | gttcctctcc | actataattt | gtacaatgca | 900 |
| tctaatagcg | gtggttatta | tgatatgaga | aatatttaaa | atggttctgt | ggtgcaaaaa | 960 |
| catccaacac | atgccgttac | ttttgttgat | aaccatgatt | ctcagcccgg | ggaagcattg | 1020 |
| gaatcctttg | ttcaacaatg | gtttaaacca | cttgcatatg | cattggttct | gacaagggaa | 1080 |
| caaggttatc | cttccgtatt | ttatgggat | tactacggta | tcccaaccca | tggtgttccg | 1140 |

```
gctatgaaat ctaaaataga ccctcttctg caggcacgtc aaactttttgc ctatggtacg    1200 cagcatgatt actttgatca tcatgatatt atcggttgga caagagaggg aaatagctcc    1260
catccaaatt caggccttgc caccattatg tcagatggtc caggtggtaa caaatggatg    1320
tatgtgggga aaaataaagc gggacaagtt tggagagata ttaccggaaa taggacaggc    1380
accgtcacaa ttaatgcaga cggatgggt aatttctctg ttaatggagg gtccgtttcg    1440
gtttgggtga agcaa                                                      1455
```

<210> SEQ ID NO 14
<211> LENGTH: 1455
<212> TYPE: DNA
<213> ORGANISM: Bacillus sp.

<400> SEQUENCE: 14

```
catcataatg ggacaaatgg gacgatgatg caatactttg aatggcactt gcctaatgat     60
gggaatcact ggaatagatt aagagatgat gctagtaatc taagaaatag aggtataacc    120
gctatttgga ttccgcctgc ctggaaaggg acttcgcaaa atgatgtggg gtatggagcc    180
tatgatcttt atgatttagg ggaatttaat caaaagggga cggttcgtac taagtatggg    240
acacgtagtc aattggagtc tgccatccat gctttaaaga ataatggcgt tcaagtttat    300
ggggatgtag tgatgaacca taaggagga gctgatgcta cagaaaacgt tcttgctgtc    360
gaggtgaatc caaataaccg gaatcaagaa atatctgggg actacacaat tgaggcttgg    420
actaagtttg attttccagg gagggtaat acatactcag actttaaatg gcgttggtat    480
catttcgatg tgtagattg ggatcaatca cgacaattcc aaaatcgtat ctacaaattc    540
cgaggtgatg gtaaggcatg ggattgggaa gtagattcgg aaaatggaaa ttatgattat    600
ttaatgtatg cagatgtaga tatggatcat ccggaggtag taaatgagct tagaagatgg    660
ggagaatggt atacaaatac attaaatctt gatggattta ggatcgatgc ggtgaagcat    720
attaaatata gctttacacg tgattggttt acccatgtaa gaaacgcaac gggaaaagaa    780
atgtttgctg ttgctgaatt ttggaaaaat gatttaggtg ccttggagaa ctattttaat    840
aaaacaaact ggaatcattc tgtctttgat gtcccccttc attataatct ttataacgcg    900
tcaaatagtg gaggcaacta tgacatggca aaacttctta atggaacggt tgttcaaaag    960
catccaatgc atgccgtaac ttttgtggat aatcacgatt ctcaacctgg ggaatcatta   1020
gaatcatttg tacaagaatg gtttaagcca cttgcttatg cgcttatttt aacaagagaa   1080
caaggctatc cctctgtctt ctatggtgac tactatggaa ttccaacaca tagtgtccca   1140
gcaatgaaag ccaagattga tccaatctta gaggcgcgtc aaaattttgc atatggaaca   1200
caacatgatt attttgacca tcataatata tcggatgga cacgtgaagg aaataccacg   1260
catcccaatt caggacttgc gactatcatg tcggatgggc caggggggag aaatggatg   1320 tacgtagggc aaaataaagc aggtcaagtt tggcatgaca taactggaaa taaaccagga   1380
acagttacga tcaatgcaga tggatggct aattttttcag taaatggagg atctgtttcc   1440
atttgggtga aacga                                                     1455
```

<210> SEQ ID NO 15
<211> LENGTH: 60
<212> TYPE: DNA
<213> ORGANISM: Artifiicial sequence
<220> FEATURE:
<223> OTHER INFORMATION: primer

<400> SEQUENCE: 15
caaaatcgta tctacaaatt cmrkrsyarg dvktgggatt sggaagtaga ttcggaaaat    60

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gaatttgtag atacgatttt g                                              21

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
cgattgctga cgctgttatt tgcg                                           24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
cttgttccct tgtcagaacc aatg                                           24

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
gtcatagttg ccgaaatctg tatcgacttc                                     30

<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20
cccagtccca cgtacgtccc ctgaatttat atattttg                            38

<210> SEQ ID NO 21
<211> LENGTH: 38
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: n on position 12 is 25% A, 25% C, 25% G, 25% T
      Primer

<400> SEQUENCE: 21
cccagtccca gntctttccc ctgaatttat atattttg                            38

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
gcgtggacaa agtttgattt tcctg                                    25

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
cctaatgatg ggaatcactg g                                        21

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gcattggatg cttttgaaca accg                                     24

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
cgcaaaatga tatcgggtat ggagcc                                   26

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
gtgatgaacc acswaggtgg agctgatgc                                29

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
gatggtgtat ggrycaatca cgacaattcc                               30

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
ggtgtatggg ataactcacg acaattcc                                    28

<210> SEQ ID NO 29
<211> LENGTH: 28
<212> TYPE: DNA
<213> ORGANISM: Artificial Sequence
<220> FEATURE:
<223> OTHER INFORMATION: Primer

<400> SEQUENCE: 29
ggtgtatggg atctctcacg acaattcc                                    28

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30
gggatcaatc acgaaatttc caaaatcgta tc                               32

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
gggatcaatc acgactcttc caaaatcgta tc                               32

<210> SEQ ID NO 32
<211> LENGTH: 34
<212> TYPE: DNA
<213> ORGANISM: Artificial Sequence
<220> FEATURE:
<223> OTHER INFORMATION: Primer

<400> SEQUENCE: 32
ggaaattatg attatatcat gtatgcagat gtag                             34

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
gctgaatttt ggtcgaatga tttaggtgcc                                  30

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
gctgaatttt ggtcgaatga tttaggtgcc                                  30

<210> SEQ ID NO 35

```
<211> LENGTH: 27
<212> TYPE: DNA
<213> ORGANISM: Artificial Sequence
<220> FEATURE:
<223> OTHER INFORMATION: Primer

<400> SEQUENCE: 35
gaattttgga agtacgattt aggtcgg                                           27

<210> SEQ ID NO 36
<211> LENGTH: 29
<212> TYPE: DNA
<213> ORGANISM: Artificial Sequence
<220> FEATURE:
<223> OTHER INFORMATION: Primer

<400> SEQUENCE: 36
ggaaaaacga trycggtgcc ttggagaac                                         29

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
gatttaggtg cctrycagaa ctattta                                           27

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
cccccttcat gagaatcttt ataacg                                            26

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
gaatccgaac ctcattacac attcg                                             25

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
cggatggact cgagaaggaa ataccacg                                          28

<210> SEQ ID NO 41
<211> LENGTH: 31
<212> TYPE: DNA
<213> ORGANISM: Artificial Sequence
<220> FEATURE:
<223> OTHER INFORMATION: Primer

<400> SEQUENCE: 41
```

-continued cgtagggcaa aatcaggccg gtcaagtttg g    31

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
cataactgga aatcgcccgg gaacagttac g    31

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
ctggaaataa awccggaaca gttacg    26

<210> SEQ ID NO 44
<211> LENGTH: 32
<212> TYPE: DNA
<213> ORGANISM: Artificial Sequence
<220> FEATURE:
<223> OTHER INFORMATION: Primer

<400> SEQUENCE: 44
ggaaataaac caggaccctgt tacgatcaat gc    32

<210> SEQ ID NO 45
<211> LENGTH: 28
<212> TYPE: DNA
<213> ORGANISM: Artificial Sequence
<220> FEATURE:
<223> OTHER INFORMATION: Primer

<400> SEQUENCE: 45
gaggcttgga ctaggtttga ttttccag    28

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
gctgaatttt ggcgcaatga tttaggtgcc    30

<210> SEQ ID NO 47
<211> LENGTH: 34
<212> TYPE: DNA
<213> ORGANISM: Artificial Sequence
<220> FEATURE:
<223> OTHER INFORMATION: Primer

<400> SEQUENCE: 47
gtgtttgacg tcccgcttca tgagaattta cagg    34

<210> SEQ ID NO 48
<211> LENGTH: 34
<212> TYPE: DNA

<213> ORGANISM: Artificial Sequence
<220> FEATURE:
<223> OTHER INFORMATION: Primer

<400> SEQUENCE: 48
gtgtttgacg tcccgcttca taagaattta cagg                          34

<210> SEQ ID NO 49
<211> LENGTH: 34
<212> TYPE: DNA
<213> ORGANISM: Artificial Sequence
<220> FEATURE:
<223> OTHER INFORMATION: Primer

<400> SEQUENCE: 49
gtgtttgacg tcccgcttca tgccaattta cagg                          34

<210> SEQ ID NO 50
<211> LENGTH: 32
<212> TYPE: DNA
<213> ORGANISM: Artificial Sequence
<220> FEATURE:
<223> OTHER INFORMATION: Primer

<400> SEQUENCE: 50
agggaatccg gatacccctga ggttttctac gg                           32

<210> SEQ ID NO 51
<211> LENGTH: 34
<212> TYPE: DNA
<213> ORGANISM: Artificial Sequence
<220> FEATURE:
<223> OTHER INFORMATION: Primer

<400> SEQUENCE: 51
gatgtggttt tggatcataa ggccggcgct gatg                          34

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
ctgttattaa tgccgccaaa cc                                       22

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
ggaaaagaaa tgtttacggt tgcg                                     24

<210> SEQ ID NO 54
<211> LENGTH: 25
<212> TYPE: DNA
<213> ORGANISM: Artificial Sequence
<220> FEATURE:
<223> OTHER INFORMATION: Primer

<400> SEQUENCE: 54
gaaatgaagc ggaacatcaa acacg                                    25

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gtatgattta ggagaattcc                                              20

<210> SEQ ID NO 56
<211> LENGTH: 33
<212> TYPE: DNA
<213> ORGANISM: Artificial Sequence
<220> FEATURE:
<223> OTHER INFORMATION: Primer

<400> SEQUENCE: 56
ccagcgcgcc taggtcacgc tgccaatatt cag                               33

<210> SEQ ID NO 57
<211> LENGTH: 33
<212> TYPE: DNA
<213> ORGANISM: Artificial Sequence
<220> FEATURE:
<223> OTHER INFORMATION: Primer

<400> SEQUENCE: 57
ccagcgcgcc taggtcatcc tgccaatatt cag                               33

<210> SEQ ID NO 58
<211> LENGTH: 2084
<212> TYPE: DNA
<213> ORGANISM: Bacillus amyloliquefaciens
<220> FEATURE:
<221> NAME/KEY: CDS
<222> LOCATION: (343)...(1794)

<400> SEQUENCE: 58
gccccgcaca tacgaaaaga ctggctgaaa acattgagcc tttgatgact gatgatttgg    60
ctgaagaagt ggatcgattg tttgagaaaa gaagaagacc ataaaaatac cttgtctgtc   120
atcagacagg gtattttta tgctgtccag actgtccgct gtgtaaaaat aaggaataaa   180 gggggttgt tattattta ctgatatgta aaatataatt tgtataagaa aatgagaggg    240
agaggaaaca tgattcaaaa acgaaagcgg acagtttcgt tcagacttgt gcttatgtgc   300
acgctgttat ttgtcagttt gccgattaca aaaacatcag cc gta aat ggc acg      354
                                                Val Asn Gly Thr
                                                  1 ctg atg cag tat ttt gaa tgg tat acg ccg aac gac ggc cag cat tgg     402
Leu Met Gln Tyr Phe Glu Trp Tyr Thr Pro Asn Asp Gly Gln His Trp
  5              10                  15                  20 aaa cga ttg cag aat gat gcg gaa cat tta tcg gat atc gga atc act     450
Lys Arg Leu Gln Asn Asp Ala Glu His Leu Ser Asp Ile Gly Ile Thr
             25                  30                  35 gcc gtc tgg att cct ccc gca tac aaa gga ttg agc caa tcc gat aac     498
Ala Val Trp Ile Pro Pro Ala Tyr Lys Gly Leu Ser Gln Ser Asp Asn
         40                  45                  50 gga tac gga cct tat gat ttg tat gat tta gga gaa ttc cag caa aaa     546
Gly Tyr Gly Pro Tyr Asp Leu Tyr Asp Leu Gly Glu Phe Gln Gln Lys
     55                  60                  65 ggg acg gtc aga acg aaa tac ggc aca aaa tca gag ctt caa gat gcg     594

```
Gly Thr Val Arg Thr Lys Tyr Gly Thr Lys Ser Glu Leu Gln Asp Ala
     70                  75                  80 atc ggc tca ctg cat tcc cgg aac gtc caa gta tac gga gat gtg gtt        642
Ile Gly Ser Leu His Ser Arg Asn Val Gln Val Tyr Gly Asp Val Val
 85                  90                  95                 100 ttg aat cat aag gct ggt gct gat gca aca gaa gat gta act gcc gtc        690
Leu Asn His Lys Ala Gly Ala Asp Ala Thr Glu Asp Val Thr Ala Val
                    105                 110                 115 gaa gtc aat ccg gcc aat aga aat cag gaa act tcg gag gaa tat caa        738
Glu Val Asn Pro Ala Asn Arg Asn Gln Glu Thr Ser Glu Glu Tyr Gln
                120                 125                 130 atc aaa gcg tgg acg gat ttt cgt ttt ccg ggc cgt gga aac acg tac        786
Ile Lys Ala Trp Thr Asp Phe Arg Phe Pro Gly Arg Gly Asn Thr Tyr
            135                 140                 145 agt gat ttt aaa tgg cat tgg tat cat ttc gac gga gcg gac tgg gat        834
Ser Asp Phe Lys Trp His Trp Tyr His Phe Asp Gly Ala Asp Trp Asp
150                 155                 160 gaa tcc cgg aag atc agc cgc atc ttt aag ttt cgt ggg gaa gga aaa        882
Glu Ser Arg Lys Ile Ser Arg Ile Phe Lys Phe Arg Gly Glu Gly Lys
165                 170                 175                 180 gcg tgg gat tgg gaa gta tca agt gaa aac ggc aac tat gac tat tta        930
Ala Trp Asp Trp Glu Val Ser Ser Glu Asn Gly Asn Tyr Asp Tyr Leu
                    185                 190                 195 atg tat gct gat gtt gac tac gac cac cct gat gtc gtg gca gag aca        978
Met Tyr Ala Asp Val Asp Tyr Asp His Pro Asp Val Val Ala Glu Thr
                200                 205                 210 aaa aaa tgg ggt atc tgg tat gcg aat gaa ctg tca tta gac ggc ttc       1026
Lys Lys Trp Gly Ile Trp Tyr Ala Asn Glu Leu Ser Leu Asp Gly Phe
            215                 220                 225 cgt att gat gcc gcc aaa cat att aaa ttt tca ttt ctg cgt gat tgg       1074
Arg Ile Asp Ala Ala Lys His Ile Lys Phe Ser Phe Leu Arg Asp Trp
        230                 235                 240 gtt cag gcg gtc aga cag gcg acg gga aaa gaa atg ttt acg gtt gcg       1122
Val Gln Ala Val Arg Gln Ala Thr Gly Lys Glu Met Phe Thr Val Ala
245                 250                 255                 260 gag tat tgg cag aat aat gcc ggg aaa ctc gaa aac tac ttg aat aaa       1170
Glu Tyr Trp Gln Asn Asn Ala Gly Lys Leu Glu Asn Tyr Leu Asn Lys
                    265                 270                 275 aca agc ttt aat caa tcc gtg ttt gat gtt ccg ctt cat ttc aat tta       1218
Thr Ser Phe Asn Gln Ser Val Phe Asp Val Pro Leu His Phe Asn Leu
                280                 285                 290 cag gcg gct tcc tca caa gga ggc gga tat gat atg agg cgt ttg ctg       1266
Gln Ala Ala Ser Ser Gln Gly Gly Gly Tyr Asp Met Arg Arg Leu Leu
            295                 300                 305 gac ggt acc gtt gtg tcc agg cat ccg gaa aag gcg gtt aca ttt gtt       1314
Asp Gly Thr Val Val Ser Arg His Pro Glu Lys Ala Val Thr Phe Val
        310                 315                 320 gaa aat cat gac aca cag ccg gga cag tca ttg gaa tcg aca gtc caa       1362
Glu Asn His Asp Thr Gln Pro Gly Gln Ser Leu Glu Ser Thr Val Gln
325                 330                 335                 340 act tgg ttt aaa ccg ctt gca tac gcc ttt att ttg aca aga gaa tcc       1410
Thr Trp Phe Lys Pro Leu Ala Tyr Ala Phe Ile Leu Thr Arg Glu Ser
                    345                 350                 355 ggt tat cct cag gtg ttc tat ggg gat atg tac ggg aca aaa ggg aca       1458
Gly Tyr Pro Gln Val Phe Tyr Gly Asp Met Tyr Gly Thr Lys Gly Thr
                360                 365                 370 tcg cca aag gaa att ccc tca ctg aaa gat aat ata gag ccg att tta       1506
Ser Pro Lys Glu Ile Pro Ser Leu Lys Asp Asn Ile Glu Pro Ile Leu
            375                 380                 385
```

-continued

```
aaa gcg cgt aag gag tac gca tac ggg ccc cag cac gat tat att gac    1554
Lys Ala Arg Lys Glu Tyr Ala Tyr Gly Pro Gln His Asp Tyr Ile Asp
    390             395                 400 cac ccg gat gtg atc gga tgg acg agg gaa ggt gac agc tcc gcc gcc    1602
His Pro Asp Val Ile Gly Trp Thr Arg Glu Gly Asp Ser Ser Ala Ala
405                 410                 415                 420 aaa tca ggt ttg gcc gct tta atc acg gac gga ccc ggc gga tca aag    1650
Lys Ser Gly Leu Ala Ala Leu Ile Thr Asp Gly Pro Gly Gly Ser Lys
                425                 430                 435 cgg atg tat gcc ggc ctg aaa aat gcc ggc gag aca tgg tat gac ata    1698
Arg Met Tyr Ala Gly Leu Lys Asn Ala Gly Glu Thr Trp Tyr Asp Ile
                440                 445                 450 acg ggc aac cgt tca gat act gta aaa atc gga tct gac ggc tgg gga    1746
Thr Gly Asn Arg Ser Asp Thr Val Lys Ile Gly Ser Asp Gly Trp Gly
        455                 460                 465 gag ttt cat gta aac gat ggg tcc gtc tcc att tat gtt cag aaa taa    1794
Glu Phe His Val Asn Asp Gly Ser Val Ser Ile Tyr Val Gln Lys
        470                 475                 480 ggtaataaaa aaacacctcc aagctgagtg cgggtatcag cttggaggtg cgtttatttt    1854
ttcagccgta tgacaaggtc ggcatcaggt gtgacaaata cggtatgctg gctgtcatag    1914
gtgacaaatc cggtttttgc gccgtttggc tttttcacat gtctgatttt tgtataatca    1974
acaggcacgg agccggaatc tttcgccttg gaaaaataag cggcgatcgt agctgcttcc    2034
aatatggatt gttcatcggg atcgctgctt ttaatcacaa cgtgggatcc              2084
```